US010525107B2

(12) United States Patent
Bell et al.

(10) Patent No.: US 10,525,107 B2
(45) Date of Patent: Jan. 7, 2020

(54) BLOOD PLASMA FRACTIONS AS A TREATMENT FOR AGING-ASSOCIATED COGNITIVE DISORDERS

(71) Applicant: Alkahest, Inc., San Carlos, CA (US)

(72) Inventors: David Bell, Dublin (IE); Ian Gallager, Half Moon Bay, CA (US); Steven P. Braithwaite, Redwood City, CA (US); S. Sakura Minami, San Francisco, CA (US); Vu Dang, San Mateo, CA (US); Joe McCracken, Hillsborough, CA (US); Karoly Nikolich, Emerald Hills, CA (US)

(73) Assignee: Alkahest, Inc., San Carlos, CA (US)

( * ) Notice: Subject to any disclaimer, the term of this patent is extended or adjusted under 35 U.S.C. 154(b) by 0 days.

(21) Appl. No.: 15/499,694

(22) Filed: Apr. 27, 2017

(65) Prior Publication Data
US 2018/0110839 A1    Apr. 26, 2018

Related U.S. Application Data

(60) Provisional application No. 62/412,258, filed on Oct. 24, 2016, provisional application No. 62/376,529, filed on Aug. 18, 2016.

(51) Int. Cl.
*A61K 38/38* (2006.01)
*A61K 35/16* (2015.01)

(52) U.S. Cl.
CPC ............ *A61K 38/385* (2013.01); *A61K 35/16* (2013.01)

(58) Field of Classification Search
CPC ... A61K 38/1709; A61K 38/385; A61P 25/28; G01N 2800/2821; G01N 33/6896
See application file for complete search history.

(56) References Cited

U.S. PATENT DOCUMENTS

| | | | | |
|---|---|---|---|---|
| 4,075,197 | A * | 2/1978 | Schuck | C07K 14/765 530/364 |
| 4,624,768 | A * | 11/1986 | Yoshida | G01N 27/44708 204/616 |
| 4,900,720 | A | 2/1990 | Kotitschke | |
| 5,916,202 | A | 6/1999 | Haswell | |
| 6,632,174 | B1 | 10/2003 | Breznitz | |
| 6,946,546 | B2 | 9/2005 | Vaughan et al. | |
| 7,785,601 | B2 | 8/2010 | Schaebitz et al. | |
| 7,851,446 | B2 * | 12/2010 | Roura | A61K 38/38 514/1.1 |
| 2002/0143283 | A1 | 10/2002 | Braverman et al. | |
| 2002/0151064 | A1 | 10/2002 | Rothenberg et al. | |
| 2003/0157687 | A1 | 8/2003 | Greene et al. | |
| 2004/0120937 | A1 | 6/2004 | Wilson | |
| 2004/0127445 | A1 | 7/2004 | Liew et al. | |
| 2004/0141946 | A1 | 7/2004 | Schaebitz et al. | |
| 2004/0146565 | A1 * | 7/2004 | Strohbehn | A61K 9/14 424/530 |
| 2004/0254152 | A1 | 12/2004 | Monje et al. | |
| 2005/0221348 | A1 | 10/2005 | Ray et al. | |
| 2006/0094064 | A1 | 5/2006 | Ray et al. | |
| 2006/0198851 | A1 | 9/2006 | Basi et al. | |
| 2006/0263759 | A1 | 11/2006 | Alves-Filho et al. | |
| 2007/0037200 | A1 | 2/2007 | Ray et al. | |
| 2007/0155725 | A1 | 7/2007 | Li et al. | |
| 2007/0190055 | A1 | 8/2007 | Ambati | |
| 2008/0026485 | A1 | 1/2008 | Hueber et al. | |
| 2008/0057590 | A1 | 3/2008 | Urdea et al. | |
| 2009/0111740 | A1 | 4/2009 | Grifols Roura | |
| 2009/0143394 | A1 | 6/2009 | Wyss-Coray et al. | |
| 2009/0181008 | A1 | 7/2009 | Ray et al. | |
| 2009/0239241 | A1 | 9/2009 | Ray et al. | |
| 2010/0080850 | A1 | 4/2010 | Hubbel et al. | |
| 2010/0124756 | A1 | 5/2010 | Ray et al. | |
| 2010/0258496 | A1 | 10/2010 | Hidaka et al. | |
| 2010/0310609 | A1 | 12/2010 | Watson et al. | |
| 2010/0324079 | A1 | 12/2010 | Ohyagi | |
| 2011/0117100 | A1 | 5/2011 | Britschgi et al. | |
| 2011/0202284 | A1 | 8/2011 | McReynolds et al. | |
| 2011/0212854 | A1 | 9/2011 | Ray et al. | |
| 2011/0243947 | A1 | 10/2011 | Doody et al. | |
| 2012/0095000 | A1 | 4/2012 | Wyss-Coray et al. | |
| 2012/0258075 | A1 | 10/2012 | Wyss-Coray et al. | |
| 2013/0040844 | A1 | 2/2013 | Wyss-Coray et al. | |
| 2013/0102537 | A1 * | 4/2013 | Bairstow | A61K 38/1709 514/15.3 |
| 2013/0302322 | A1 | 11/2013 | Wong et al. | |
| 2014/0011689 | A1 | 1/2014 | Sandip et al. | |

(Continued)

FOREIGN PATENT DOCUMENTS

| | | |
|---|---|---|
| EP | 19930184040 B1 | 4/1993 |
| EP | 2111868 B1 | 8/2013 |

(Continued)

OTHER PUBLICATIONS

Albumin (Human) U.S.P. 2012 (Year: 2012).*
Plasma protein fraction (human). Bayer 2002, pp. 1-5. (Year: 2002).*
FDA 21 CFR 640.92. 2001. (Year: 2001).*
Conboy et al., "Heterochronic parabiosis for the study of the effects of aging on stem cells and their niches." Cell Cycle. 2012. pp. 2260-2268.
Conboy et al., "Heterochronic parabiosis: Historical perspective and methodological considerations for studies of aging and longevity," Aging Cell, available online Apr. 2013. pp. 525-530.
Conboy et al., "Rejuvination of aged progenitor cells by exposure to a young systemic environment." Nature. 2005. pp. 760-764.
Katcher, "Studies that Shed New Light on Aging." Biochemistry (Moscow), Sep. 2013. pp. 1061-1070.

(Continued)

*Primary Examiner* — Marcela M Cordero Garcia
*Assistant Examiner* — Jia-Hai Lee
(74) *Attorney, Agent, or Firm* — Bret E. Field; Bozicevic, Field & Francis LLP

(57) ABSTRACT

Methods and compositions for treating and/or preventing aging-related conditions are described. The compositions used in the methods include fractions derived from blood plasma with efficacy in treating and/or preventing aging-related conditions such as neurocognitive disorders.

8 Claims, 23 Drawing Sheets

(56) References Cited

U.S. PATENT DOCUMENTS

| | | |
|---|---|---|
| 2014/0121438 A1 | 6/2014 | Quirk |
| 2014/0255424 A1 | 9/2014 | Wyss-Coray et al. |
| 2015/0079045 A1 | 3/2015 | Kong |
| 2015/0157664 A1* | 6/2015 | Wyss-Coray .......... A61K 35/16 424/530 |
| 2016/0143996 A1 | 5/2016 | Wyss-Coray et al. |
| 2016/0208011 A1 | 7/2016 | Wyss-Coray et al. |
| 2017/0081415 A1 | 3/2017 | Wong et al. |
| 2017/0232118 A1 | 8/2017 | Wyss-Coray et al. |

FOREIGN PATENT DOCUMENTS

| | | |
|---|---|---|
| RU | 2428997 C1 | 9/2011 |
| RU | 2470677 C1 | 12/2012 |
| UA | 35656 C2 | 4/2001 |
| WO | WO2005052592 A2 | 6/2005 |
| WO | WO2005106492 A2 | 11/2005 |
| WO | WO2006133423 A1 | 12/2006 |
| WO | WO2007059135 A2 | 5/2007 |
| WO | WO2009023814 A2 | 2/2009 |
| WO | WO2009055729 A1 | 4/2009 |
| WO | WO2011094535 A2 | 8/2011 |
| WO | WO2013142135 A1 | 9/2013 |
| WO | WO2015088915 A1 | 6/2015 |
| WO | WO2016187217 A2 | 11/2016 |
| WO | WO2016205004 A2 | 12/2016 |
| WO | WO2017120461 A1 | 7/2017 |

OTHER PUBLICATIONS

Loffredo et al., "Growth Differentiation Factor 11 is a Circulating Factor that Reverses Age-Related Cardiac Hypertrophy." Cell. May 2013. pp. 828-839.

Krementsov, "A Martian Stranded on Earth: Alexander Bogdanov, Blood Transfusions, and Proletarian Science." pp. 57-59, 85, 86, and 88. University of Chicago Press, Chicago, United States, 2011.

Boada et al., "Treatment of Alzheimer disease using combination therapy with plasma exchange and haemapheresis with albumin and intravenous immunoglobulin: Rationale and treatment approach of the AMBAR (Alzheimer Management by Albumin Replacement) study." Neurologia, vol. 31, No. 7, pp. 473-481 (Jul. 29, 2016). See abstract; p. 479.

Hughes et al., "Clinical applications of intravenous immunoglobulins in neurology." Clinical and Experimental Immunology, vol. 158, supple.1, pp. 34-42 (2009). See abstract; pp. 38-40.

Website document entitled "Plasma Protein Composition" (available at http://www.sigmaaldrich.com/life-science/metabolomics/enzyme-explorer/learning-center/plasma-blood-proteins/plasma-protein-composition.html). Downloaded on Jun. 27, 2017.

"Young blood can reverse some effects of ageing, study finds," Society for Neuroscience, The Observer, Oct. 24, 2012, 2 pages, Retrieved online: http://gonzoj.wordpress.com/tag/society-for-neuroscience/.

Adair et al., "Measurement of gelatinase B (MMP-9) in the cerebrospinal fluid of patients with vascular dementia and Alzheimer disease." Stroke. Jun. 2004;35(6):e159-62.

Adkins et al., "Toward a Human Blood Serum Proteome", (2002) Molecular & Cellular Proteomics 1: 947-955.

Anderson et al., "The Human Plasma Proteome", (2002) Molecular & Cellular Proteomics 1: 845-867.

Anderson et al., "High resolution two-dimensional electrophoresis of human plasma proteins", (1977) Proc. Natl. Acad. Sci. vol. 74, No. 12, pp. 5421-5425.

Baba et al., "Timp-3 deficiency impairs cognitive function in mice." Lab Invest. Dec. 2009;89(12):1340-7.

Berezovskaya et al., "Colony stimulating factor-1 potentiates neuronal survival in cerebral cortex ischemic lesion." Acta Neuropathol. Nov. 1996;92(5):479-86.

Boissonneault et al., "Powerful beneficial effects of macrophage colony-stimulating factor on beta-amyloid deposition and cognitive impairment in Alzheimer's disease." Brain. Apr. 2009;132(Pt 4):1078-92.

Bouchard et al., "Aging and brain rejuvenation as systemic events," J. Neurochem. Jan. 2015; 132(1):5-19.

Britschgi et al., "Blood protein signature for the early diagnosis of Alzheimer disease." Arch Neurol. Feb. 2009;66(2):161-5.

Cheung et al., "Serum β-2 microglobulin predicts mortality in people with diabetes." Eur J Endocrinol. May 17, 2013;169(1):1-7.

Fedoroff et al., "Role of colony stimulating factor-1 in brain damage caused by ischemia." Neurosci Biobehav Rev. Mar. 1997;21(2):187-91.

Gowing et al., "Macrophage colony stimulating factor (M-CSF) exacerbates ALS disease in a mouse model through altered responses of microglia expressing mutant superoxide dismutase." Exp Neurol. Dec. 2009;220(2):267-75.

Jha, "Young blood can reverse some effects of ageing, study finds," The Guardian, Oct. 17, 2012, 4 pages.

Kwak et al., "Aging, exercise, and extracellular matrix in the heart." J Exerc Rehabil. Jun. 30, 2013;9(3):338-47.

Lin et al., "Discovery of a cytokine and its receptor by functional screening of the extracellular proteome." Science. May 9, 2008;320(5877):807-11.

Lou et al., "Colony-stimulating factor 1 receptor (CSF1R) signaling in injured neurons facilitates protection and survival." J. Exp. Med. (2013) 210(1)157-172.

Lysaght et al., "Beta-2 microglobulin removal during continuous ambulatory peritoneal dialysis (CAPD)." Perit Dial Int. 1989;9(1):29-35.

Malkki, "Ageing: Could young blood combat age-related cognitive decline?" Nat. Rev. Neurol. Jun. 2014;10(6):307.

Manazo et al., "Role of chemokines and chemokine receptors in regulating specific leukocyte trafficking in the immune/inflammatory response." Clin Exp Rheumatol. Jul.-Aug. 2003;21(4):501-8.

McLaurin et al., "Microglial pilgrimage to the brain." Nat Med. Dec. 2010;16(12):1380-1.

Middeldorp et al., "A young systemic environment reverses degeneration in a mouse model of Alzheimer's disease," Neuroscience 2012, Presentation Abstract, Oct. 16, 2012, 2 pages.

Mitrasinovic et al., "Microglia overexpressing the macrophage colony-stimulating factor receptor are neuroprotective in a microglial-hippocampal organotypic coculture system." J Neurosci. Apr. 27, 2005;25(17):4442-51.

Mizuno et al., "Interleukin-34 selectively enhances the neuroprotective effects of microglia to attenuate oligomeric amyloid-β neurotoxicity." Am J Pathol. Oct. 2011;179(4):2016-27.

Palop et al., "A network dysfunction perspective on neurodegenerative diseases." Nature. Oct. 19, 2006;443 (7113):768-73.

Prakasam et al., "Amyloid and neurodegeneration: Alzheimer's disease and retinal degeneration." Chapter 7, Handbook of Neurochemistry and Molecular Neurobiology, Lajtha ed., 2009, 131-163. (Year: 2009).

Ron-Harel et al., "Age-Dependent Spatial Memory Loss Can Be Partially Restored by Immune Activation," Rejuvenation Resarch (2008), 11(5):903-13.

Royer et al., "A novel antagonist of prostaglandin 02 blocks the locomotion of eosinophils and basophils." Eur J Clin nvestl Sep. 2008;38(9):663-71.

Schwartz et al., "How Do Immune Cells Support and Shape the Brain in Health, Disease, and Aging?" The Journal of Neuroscience, Nov. 6, 2013, 33(45):17587-96.

Sellebjerg et al., "Identification of new sensitive biomarkers for the in vivo response to interferon-beta treatment in multiple sclerosis using DNA-array evaluation." Eur J Neurol. Dec. 2009;16(12):1291-8.

Shin et al., "Association of eotaxin gene family with asthma and serum total IgE." Hum Mol Genet. Jun. 1, 2003;12(11)1279-85.

Skovronsky et al., "Neurodegenerative diseases: new concepts of pathogenesis and their therapeutic implications." Annu Rev Pathol. 2006;1:151-70.

Smith et al., "β2-microglobulin is a systemic pro-aging factor that impairs cognitive function and neurogenesis." Nat Med. Aug. 2015;21(8):932-7.

(56) References Cited

OTHER PUBLICATIONS

Strobel et al., "Chicago: the vampire principle—young blood rejuvenates aging brain?" Alzheimer Research Forum (Nov. 2009), p. 1-3.
Stubbs et al., "Indomethacin causes prostaglandin 0(2)-like and eotaxin-like selective responses in eosinophils and basophils." J Biol Chem. Jul. 19, 2002;277(29):26012-20.
Teixeira et al., "Increased serum levels of CCL 11/eotaxin in schizophrenia," "Process in neuro-psychopharmacology & biological psychiatry," vol. 32, No. 3, pp. 710-714, 2008.
Thomson et al., "Young blood for a keener mind," New Scientist (2012), 216(2887): 10.
Villeda et al., "Changes in the systemic milieu modulate neurogenesis during aging." Abstract, 39th Annual Neuroscience Meeting, Chicago, IL, Society for Neuroscience, Oct. 2009, 1-2. (Year: 2009).
Villeda et al., "The aging systemic milieu negatively regulates neurogenesis and cognitive function," Nature, Aug. 31, 2011, 477(7362):90-4.
Villeda et al., "Young blood reverses age-related cognitive impairments," Neuroscience 2012, Presentation Abstract, Oct. 17, 2012, 2 pages.
Villeda et al., "Young blood reverses age-related impairments in cognitive function and synaptic plasticity in mice," Nat Med. (Jun. 2014), 20(6):659-63.
Vincent et al., "Macrophage colony stimulating factor prevents NMDA-induced neuronal death in hippocampal organotypic cultures." J Neurochem. Sep. 2002;82(6):1388-97.

Wang et al., "Expression of colony stimulating factor-1 receptor (CSF-1R) by CNS neurons in mice." J Neurosci Res. Sep. 1, 1999;57(5):616-32.
Wang et al., "Matrix metalloproteinases and their multiple roles in Alzheimer's disease." Biomed Res Int. 2014;2014:908636.
Wilson et al., "Beta2-microglobulin as a biomarker in peripheral arterial disease: proteomic profiling and clinical studies." Circulation. Sep. 18, 2007;116(12):1396-403.
Yagihashi et al., "Macrophage colony stimulating factor (M-CSF) protects spiral ganglion neurons following auditory nerve injury: morphological and functional evidence." Exp Neurol. Mar. 2005;192(1):167-77.
Yamane et al., "CSF-1 receptor-mediated differentiation of a new type of monocytic cell with B cell-stimulating activity: its selective dependence on IL-34." J Leukoc Biol. Jan. 2014;95(1):19-31.
Ye et al., "Haptoglobin-alpha subunit as potential serum biomarker in ovarian cancer: identification and characterization using proteomic profiling and mass spectrometry." Clinical Cancer Research (Aug. 2003), 9(8):2904-11.
Bhattacharya, "Placental umbilical cord whole blood transfusion. A safe and genuine blood substitute for patients of the under-resourced areas of this country at emergency." J Am Coll Surg. 2005. Submitted 34 pages.
Bhattacharya, "Study of the utility of placental cord blood in meeting the transfusion needs of beta-thalassaemic patients." Regional Health Forum, 2008. pp. 16-27.
Borlongan et al., "Central Nervous System Entry of Peripherally Injected Umbilical Cord Blood Cells is Not Required for Neuroprotection in Stroke." Stroke. 2004. pp. 2385-2389. Dallas, Texas.

* cited by examiner

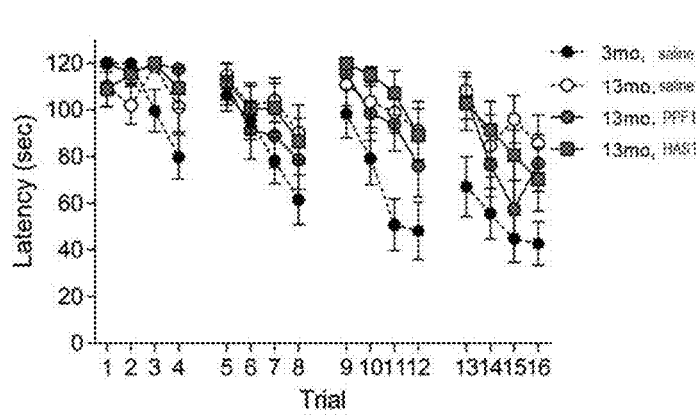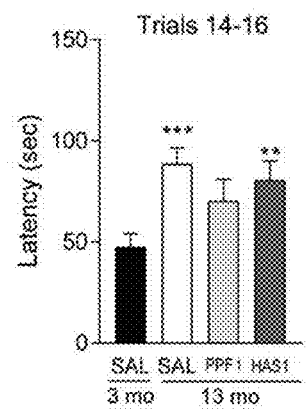
FIGURE 10A
FIGURE 10B

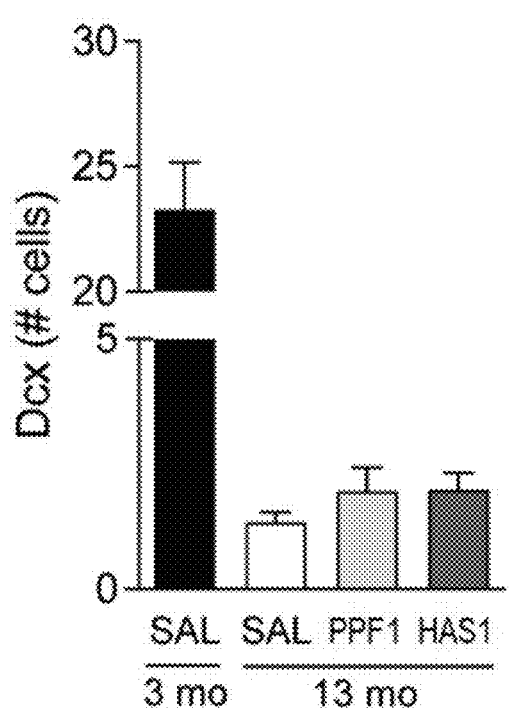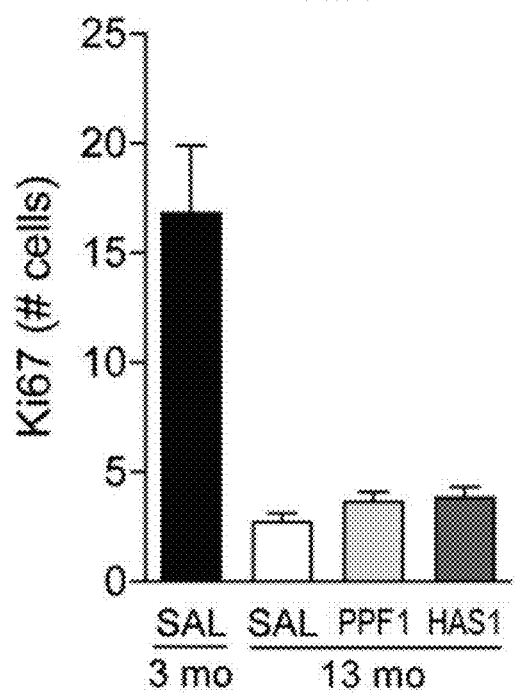

BLOOD PLASMA FRACTIONS AS A TREATMENT FOR AGING-ASSOCIATED COGNITIVE DISORDERS

CROSS REFERENCE TO RELATED APPLICATIONS

Pursuant to 35 U.S.C. § 119 (e), this application claims priority to the filing date of U.S. Provisional Patent Application No. 62/376,529, filed Aug. 18, 2016, and U.S. Provisional Patent Application No. 62/412,258, filed Oct. 24, 2016; the disclosures of which applications are herein incorporated by reference.

FIELD OF THE INVENTION

This invention pertains to the prevention and treatment of aging-associated disease. The invention relates to the use of blood products, such as blood plasma fractions, to treat and/or prevent conditions associated with aging, such as neurocognitive and neurodegenerative disorders.

BACKGROUND

The following is offered as background information only and is not admitted to be prior art to the present invention.

Aging is an important risk factor for multiple human diseases including cognitive impairment, cancer, arthritis, vision loss, osteoporosis, diabetes, cardiovascular disease, and stroke. In addition to normal synapse loss during natural aging, synapse loss is an early pathological event common to many neurodegenerative conditions, and is the best correlate to the neuronal and cognitive impairment associated with these conditions. As such, aging remains the single most dominant risk factor for dementia-related neurodegenerative diseases such as Alzheimer's disease (AD) (Bishop, N. A. et al., *Neural mechanisms of ageing and cognitive decline*. Nature 464(7288), 529-535 (2010); Heeden, T. et al., *Insights into the ageing mind: a view from cognitive neuroscience*. Nat. Rev. Neurosci. 5(2), 87-96 (2004); Mattson, M. P., et al., *Ageing and neuronal vulnerability*. Nat. Rev. Neurosci. 7(4), 278-294 (2006)). Aging affects all tissues and functions of the body including the central nervous system, and a decline in functions such as cognition, can severely impact quality of life. Treatment for cognitive decline and neurodegenerative disorders has had limited success in preventing and reversing impairment. It is therefore important to identify new treatments for maintaining cognitive integrity by protecting against, countering, or reversing the effects of aging.

SUMMARY

The present invention is based on the production and use of blood products for treating and/or preventing age-related disorders, such as cognitive impairment conditions, age-related dementia, and neurodegenerative disease. The present invention recognizes, among other things, the need for new therapies for the treatment and/or prevention of cognitive impairment, age-related dementia, and neurodegenerative disease. Derived from blood and blood plasma, the present compositions of the invention relate to a solution for the failures and shortcomings of current therapies through utilization of blood plasma fractions exhibiting efficacy in the treatment and/or prevention of cognitive impairment, age-related dementia, and neurodegenerative disease. Additionally, the current invention relates to proteins identified in blood plasma fractions which either may exhibit efficacy as treatments or preventative agents for cognitive impairment and age-related dementia themselves, or are targets for inhibition by additional agents.

The current invention also recognizes that differences in protein content between different blood plasma fractions (e.g. fractions, effluents, "Plasma Fractions," Plasma Protein Fraction, Human Albumin Solution) can be responsible for preventing and/or improving certain cognitive impairments and alleviating neurodegenerative disease. By way of example, and not limitation, embodiments of the current invention demonstrate that mere higher albumin concentration of Human Albumin Solution (HAS) preparations is not the driving force behind improved cognition associated with Plasma Protein Fraction (PPF) preparations with lower albumin concentrations.

Blood and blood plasma from young donors have exhibited improvement and reversal of the pre-existing effects of brain aging, including at the molecular, structural, functional, and cognitive levels. (Saul A. Villeda, et al. *Young blood reverses age-related impairments in cognitive function and synaptic plasticity in mice*. Nature Medicine 20 659-663 (2014)). The present invention relates to fractions and effluents of the blood plasma, some of which have been traditionally used to treat patient shock, and the discovery that they are effective as methods of treatment of aging-associated cognitive impairment.

In accordance with aspects of the invention, then, methods of treatment of aging-associated cognitive impairment, age-related dementia, and/or neurodegenerative disease using blood product fractions of blood plasma are provided. Aspects of the methods include administering a blood plasma fraction to an individual suffering from or at risk of developing aging-associated cognitive impairment or neurodegenerative disease. Additional aspects of the methods include administering a blood plasma fraction derived from a pool of donors of a specific age range to an individual suffering from or at risk of developing aging-associated cognitive impairment. Also provided are reagents, devices, and kits thereof that find use in practicing the subject methods.

In an embodiment, the blood plasma fraction may be, for example, one of several blood plasma fractions obtained from a blood fractionation process, such as the Cohn fractionation process described below. In another embodiment, the blood plasma fraction may be of the type, herein referred to as "Plasma Fraction," which is a solution comprised of normal human albumin, alpha and beta globulins, gamma globulin, and other proteins, either individually or as complexes. In another embodiment, the blood plasma fraction may be a type of blood plasma fraction known to those having skill in the art as a "Plasma Protein Fraction" (PPF). In another embodiment, the blood plasma fraction may be a "Human Albumin Solution" (HAS) fraction. In yet another embodiment, the blood plasma fraction may one in which substantially all of the clotting factors are removed in order to retain the efficacy of the fraction with reduced risk of thromboses. Embodiments of the invention may also include administering, for example, a fraction derived from a young donor or pools of young donors. Another embodiment of the invention may include the monitoring of cognitive improvement in a subject treated with a blood plasma fraction.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The accompanying drawings illustrate embodiments of the invention and, together with the description, serve to explain the invention. These drawings are offered by way of illustration and not by way of limitation: it is emphasized that the various features of the drawings may not be to-scale.

The patent or application file contains at least one drawing executed in color. Copies of this patent or patent application publication with color drawing(s) will be provided by the Office upon request and payment of the necessary fee.

FIG. 10A charts the Barnes maze latency which tests for spatial memory. The latency to reach the target hole in 3-month and 13-month-old NSG mice treated with control, PPF1, or HAS1 is reported.

FIG. 10B quantifies the average of the last 3 trials depicted in FIG. 10A.

FIG. 11A quantifies the number of cells positively staining for Doublecortin (Dcx), a marker for newborn neurons in the dentate gyrus of 3-month and 13-month-old NSG mice treated with control, PPF1, or HAS1 twice per week for up to 6 months.

FIG. 11B quantifies the number of cells positively staining for Ki67, a marker for proliferating cells in the dentate gyrus of 3-month and 13-month-old NSG mice treated with control, PPF1, or HAS1 twice per week for up to 6 months.

FIG. 21B shows the quantification of neurite length as percent of vehicle from cortices from E14-15 mouse embryos suspended in neural basal media supplemented with B27 and 2 mM Glutamax (vehicle), PPF1 (10% of a 5% stock solution), or HAS1 (10% of a 5% stock solution).

FIG. 21C shows the quantification of neurite branch points as percent of vehicle from cortices from E14-15 mouse embryos suspended in neural basal media supplemented with B27 and 2 mM Glutamax (vehicle), PPF1 (10% of a 5% stock solution), or HAS1 (10% of a 5% stock solution).

DETAILED DESCRIPTION

1. Introduction

Figure 1:
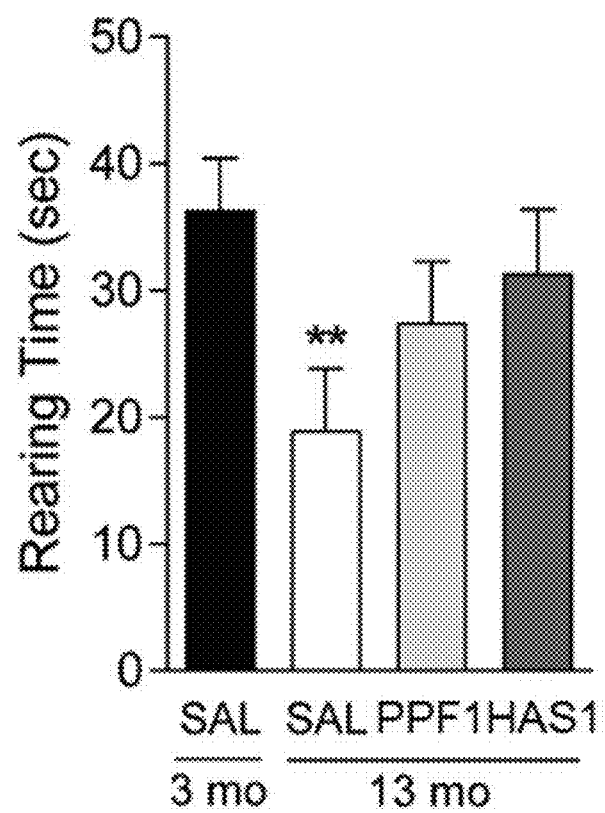
FIG. 1 shows the time spent rearing by control, PPF1, or HAS1-treated 3-month or 13-month-old NSG mice that were placed in an Open Field chamber for 15 minutes.

The present invention relates to the identification and discovery of methods and compositions for the treatment and/or prevention of cognitive impairment, including age-associated dementia and neurodegenerative disease. Described herein are methods and compositions for the treatment of subjects suffering from such disorders, which are aspects of the present invention. The methods and compositions described herein are useful in: preventing cognitive impairment, age-associated dementia, and neurodegenerative disease; ameliorating the symptoms of cognitive impairment, age-associated dementia, and neurodegenerative disease; slowing progression of aging-associated cognitive impairment, age-associated dementia, and neurodegenerative disease; and/or reversing the progression of aging-associated cognitive impairment, age-associated dementia, and neurodegenerative disease. An implementation of the invention includes using blood plasma fractions as treatment, such as one or more fractions or effluents obtained from blood fractionation processes, e.g., like the Cohn fractionation process described below. An embodiment of the invention includes using Plasma Fraction (a solution comprised of normal human albumin, alpha and beta globulins, gamma globulin, and other proteins either individually or as complexes, hereinafter referred to as "Plasma Fraction"). Another embodiment of the invention includes using Plasma Protein Fraction (PPF) as treatment. Another embodiment of the invention includes using Human Albumin Solution (HAS) fraction as treatment. Yet another embodiment includes using effluents from blood fractionation processes such as Effluent I or Effluent II/III described below. An additional embodiment includes a blood plasma fraction from which substantially all the clotting factors have been removed in order to retain efficacy while reducing the risk of thromboses (for example, see U.S. Patent Application No. 62/236,710, which is incorporated by reference in its entirety herein).

Before describing the present invention in detail, it is to be understood that this invention is not limited to a particular method or composition described, as such may, of course, vary. It is also understood that the terminology used herein is for the purpose of describing particular embodiments only, and is not intended to be limiting, since the scope of the present invention will be limited only by the appended claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

It is noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein have discrete components and features which may be readily separated from or combined with the features of any of the other several embodiments without departing from the scope or the spirit of the present invention. Any recited method can be carried out in the order of events recited or in any other order which is logically possible.

2. Definitions

Unless otherwise defined, all technical and scientific terms used herein have the same meaning as commonly understood by one having ordinary skill in the art to which the invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a," "an," and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those having skill in the art, and so forth.

In describing methods of the present invention, the terms "host", "subject", "individual" and "patient" are used interchangeably and refer to any mammal in need of such treatment according to the disclosed methods. Such mammals include, e.g., humans, ovines, bovines, equines, porcines, canines, felines, non-human primate, mice, and rats. In certain embodiments, the subject is a non-human mammal. In some embodiments, the subject is a farm animal. In other embodiments, the subject is a pet. In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). As such, subjects of the invention, include but are not limited to mammals, e.g., humans and other primates, such as chimpanzees and other apes and monkey species; and the like, where in certain embodiments the subject are humans. The term subject is also meant to include a person or organism of any age, weight or other physical characteristic, where the subjects may be an adult, a child, an infant or a newborn.

By a "young" or "young individual" it is meant an individual that is of chronological age of 40 years old or younger, e.g., 35 years old or younger, including 30 years old or younger, e.g., 25 years old or younger or 22 years old or younger. In some instances, the individual that serves as the source of the young plasma-comprising blood product is one that is 10 years old or younger, e.g., 5 years old or younger, including 1-year-old or younger. In some instances, the subject is a newborn and the source of the plasma product is the umbilical cord, where the plasma product is harvested from the umbilical cord of the newborn. As such, "young" and "young individual" may refer to a subject that is between the ages of 0 and 40, e.g., 0, 1, 5, 10, 15, 20, 25, 30, 35, or 40 years old. In other instances, "young" and "young individual" may refer to a biological (as opposed to chronological) age such as an individual who has not exhibited the levels of inflammatory cytokines in the plasma exhibited in comparatively older individuals. Conversely, these "young" and "young individual" may refer to a biological (as opposed to chronological) age such as an individual who exhibits greater levels of anti-inflammatory cytokines in the plasma compared to levels in comparatively older individuals. By way of example, and not limitation, the inflammatory cytokine is Eotaxin, and the fold difference between a young subject or young individual and older individuals is at least 20%. Similarly, the fold difference between older and younger individuals in other inflammatory cytokines may be used to refer to a biological age. (See U.S. patent application Ser. No. 13/575,437 which is herein incorporated by reference). Usually, the individual is healthy, e.g., the individual has no hematological malignancy or autoimmune disease at the time of harvest.

By "an individual suffering from or at risk of suffering from an aging-associated cognitive impairment" is meant an individual that is about more than 50% through its expected lifespan, such as more than 60%, e.g., more than 70%, such as more than 75%, 80%, 85%, 90%, 95% or even 99% through its expected lifespan. The age of the individual will depend on the species in question. Thus, this percentage is based on the predicted life-expectancy of the species in question. For example, in humans, such an individual is 50 year old or older, e.g., 60 years old or older, 70 years old or older, 80 years old or older, 90 years old or older, and usually no older than 100 years old, such as 90 years old, i.e., between the ages of about 50 and 100, e.g., 50 . . . 55 . . . 60 . . . 65 . . . 70 . . . 75 . . . 80 . . . 85 . . . 90 . . . 95 . . . 100 years old or older, or any age between 50-1000, that suffers from an aging-associated condition as further described below, e.g., cognitive impairment associated with the natural aging process; an individual that is about 50 years old or older, e.g., 60 years old or older, 70 years old or older, 80 years old or older, 90 years old or older, and usually no older than 100 years old, i.e., between the ages of about 50 and 100, e.g., 50 . . . 55 . . . 60 . . . 65 . . . 70 . . . 75 . . . 80 . . . 85 . . . 90 . . . 95 . . . 100 years old, that has not yet begun to show symptoms of an aging-associated condition e.g., cognitive impairment; an individual of any age that is suffering from a cognitive impairment due to an aging-associated disease, as described further below, and an individual of any age that has been diagnosed with an aging-associated disease that is typically accompanied by cognitive impairment, where the individual has not yet begun to show symptoms of cognitive impairment. The corresponding ages for non-human subjects are known and are intended to apply herein.

As used herein, "treatment" refers to any of (i) the prevention of the disease or disorder, or (ii) the reduction or elimination of symptoms of the disease or disorder. Treatment may be effected prophylactically (prior to the onset of disease) or therapeutically (following the onset of the disease). The effect may be prophylactic in terms of completely or partially preventing a disease or symptom thereof and/or may be therapeutic in terms of a partial or complete cure for a disease and/or adverse effect attributable to the disease. Thus, the term "treatment" as used herein covers any treatment of an aging-related disease or disorder in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. Treatment may result in a variety of different physical manifestations, e.g., modulation in gene expression, rejuvenation of tissue or organs, etc. The therapeutic agent may be administered before, during or after the onset of disease. The treatment of ongoing disease, where the treatment stabilizes or reduces the undesirable clinical symptoms of the patient, is of particular interest. Such treatment may be performed prior to complete loss of function in the affected tissues. The subject therapy may be administered during the symptomatic stage of the disease, and in some cases after the symptomatic stage of the disease.

In some embodiments, the aging-associated condition that is treated is an aging-associated impairment in cognitive ability in an individual. By cognitive ability, or "cognition," it is meant the mental processes that include attention and concentration, learning complex tasks and concepts, memory (acquiring, retaining, and retrieving new information in the short and/or long term), information processing (dealing with information gathered by the five senses), visuospatial function (visual perception, depth perception, using mental imagery, copying drawings, constructing objects or shapes), producing and understanding language, verbal fluency (word-finding), solving problems, making decisions, and executive functions (planning and prioritizing). By "cognitive decline", it is meant a progressive decrease in one or more of these abilities, e.g., a decline in memory, language, thinking, judgment, etc. By "an impairment in cognitive ability" and "cognitive impairment", it is meant a reduction in cognitive ability relative to a healthy individual, e.g., an age-matched healthy individual, or relative to the ability of the individual at an earlier point in time, e.g., 2 weeks, 1 month, 2 months, 3 months, 6 months, 1 year, 2 years, 5 years, or 10 years or more previously. By "aging-associated cognitive impairment," it is meant an impairment in cognitive ability that is typically associated with aging, including, for example, cognitive impairment associated with the natural aging process, e.g., mild cognitive impairment (M.C.I.); and cognitive impairment associated with an aging-associated disorder, that is, a disorder that is seen with increasing frequency with increasing senescence, e.g., a neurodegenerative condition such as Alzheimer's disease, Parkinson's disease, frontotemporal dementia, Huntington disease, amyotrophic lateral sclerosis, multiple sclerosis, glaucoma, myotonic dystrophy, vascular dementia, and the like.

Blood Products Comprising Plasma Components. In practicing the subject methods, a blood product comprising plasma components is administered to an individual in need thereof, e.g., an individual suffering or at risk of suffering from a cognitive impairment and/or age-related dementia. As such, methods according to embodiments of the invention including administering a blood product comprising plasma components from an individual (the "donor individual", or "donor") to an individual at least at risk of suffering or suffering from cognitive impairment and/or age-related dementia (the "recipient individual" or "recipient"). By a "blood product comprising plasma components," it is meant any product derived from blood that comprises plasma (e.g. whole blood, blood plasma, or fractions thereof). The term "plasma" is used in its conventional sense to refer to the straw-colored/pale-yellow liquid component of blood composed of about 92% water, 7% proteins such as albumin, gamma globulin, anti-hemophilic factor, and other clotting factors, and 1% mineral salts, sugars, fats, hormones and vitamins. Non-limiting examples of plasma-comprising blood products suitable for use in the subject methods include whole blood treated with anti-coagulant (e.g., EDTA, citrate, oxalate, heparin, etc.), blood products produced by filtering whole blood to remove white blood cells ("leukoreduction"), blood products consisting of plasmapheretically-derived or apheretically-derived plasma, fresh-frozen plasma, blood products consisting essentially of purified plasma, and blood products consisting essentially of plasma fractions. In some instances, plasma product that is employed is a non-whole blood plasma product, by which is meant that the product is not whole blood, such that it lacks one or more components found in whole blood, such as erythrocytes, leukocytes, etc., at least to the extent that these components are present in whole blood. In some instances, the plasma product is substantially, if not completely, acellular, where in such instances the cellular content may be 5% by volume or less, such as 1% or less, including 0.5% or less, where in some instances acellular plasma fractions are those compositions that completely lack cells, i.e., they include no cells.

Collection of blood products comprising plasma components. Embodiments of the methods described herein include administration of blood products comprising plasma components which can be derived from donors, including human volunteers. The term, "human-derived" can refer to such products. Methods of collection of plasma comprising blood products from donors are well-known in the art. (See, e.g., AABB TECHNICAL MANUAL, (Mark A. Fung, et al., eds., 18th ed. 2014), herein incorporated by reference).

In one embodiment, donations are obtained by venipuncture. In another embodiment, the venipuncture is only a single venipuncture. In another embodiment, no saline volume replacement is employed. In an embodiment, the process of plasmapheresis is used to obtain the plasma comprising blood products. Plasmapheresis can comprise the removal of a weight-adjusted volume of plasma with the return of cellular components to the donor. In the embodiment, sodium citrate is used during plasmapheresis in order to prevent cell clotting. The volume of plasma collected from a donor is preferably between 690 to 880 mL after citrate administration, and preferably coordinates with the donor's weight.

3. Blood Plasma Fractions

During the Second World War, there arose a need for a stable plasma expander which could be employed in the battlefield when soldiers lost large amounts of blood. As a result, methods of preparing freeze-dried plasma were developed. However, use of freeze-dried plasma was difficult in combat situations since reconstitution required sterile water. As an alternative, Dr. E. J. Cohn suggested that albumin could be used, and prepared a ready-to-use stable solution that could be introduced immediately for treatment of shock. (See JOHAN VANDERSANDE, CURRENT APPROACHES TO THE PREPARATION OF PLASMA FRACTIONS in (BIOTECHNOLOGY OF BLOOD) 165 (Jack Goldstein ed., 1st ed. 1991)). Dr. Cohn's procedure of purifying plasma fractions utilized cold ethanol for its denaturing effect, and employs changes in pH and temperature to achieve separation.

An embodiment of the methods described herein includes the administration of plasma fractions to a subject. Fractionation is the process by which certain protein subsets are separated from plasma. Fractionation technology is known in the art and relies on steps developed by Cohn et al. during the 1940s. (E. Cohn, *Preparation and properties of serum and plasma proteins. IV. A system for the separation into fractions of the protein and lipoprotein components of biological tissues and fluids.* 68 J Am Chem Soc 459 (1946), herein incorporated by reference). Several steps are involved in this process, each step involving specific ethanol concentrations as well as pH, temperature, and osmolality shifts which result in selective protein precipitation. Precipitates are also separated via centrifugation or precipitation. The original "Cohn fractionation process" involved separation of proteins through precipitates into five fractions, designated fraction I, fraction II+III, fraction IV-1, fraction IV-4 and fraction V. Albumin was the originally identified endpoint (fraction V) product of this process. In accordance with embodiments of the invention, each fraction (or effluent from a prior separation step) contains or potentially contains therapeutically-useful protein fractions. (See Thierry Burma, *Modern Plasma Fractionation*, 21(2) Transfusion Medicine Reviews 101 (2007); Adil Denizli, *Plasma fractionation: conventional and chromatographic methods for albumin purification*, 4 J. Biol. & Chem. 315, (2011); and T. Brodniewicz-Proba, *Human Plasma Fractionation and the Impact of New Technologies on the Use and Quality of Plasma-derived Products*, 5 Blood Reviews 245 (1991), and U.S. Pat. Nos. 3,869,431, 5,110,907, 5,219,995, 7,531,513, and 8,772,461 which are herein incorporated by reference). Adjustment of the above experimental parameters can be made in order to obtain specific protein fractions.

More recently, fractionation has reached further complexity, and as such, comprises additional embodiments of the invention. This recent increase in complexity has occurred through: the introduction of chromatography resulting in isolation of new proteins from existing fractions like cryoprecipitate, cryo-poor plasma, and Cohn fractions; increasing IgG recovery by integrating chromatography and the ethanol fractionation process; and viral reduction/inactivation/removal. (Id.) In order to capture proteins at physiological pH and ionic strength, anion-exchange chromatography can be utilized. This preserves functional activity of proteins and/or protein fractions. Heparin and monoclonal antibodies are also used in affinity chromatography. One of ordinary skill in the art would recognize that the parameters described above may be adjusted to obtain specifically-desired plasma protein-containing fractions.

In an embodiment of the invention, blood plasma is fractionated in an industrial setting. Frozen plasma is thawed at 1° C. to 4° C. Continuous refrigerated centrifugation is applied to the thawed plasma and cryoprecipitate isolated. Recovered cryoprecipitate is frozen at −30° C. or lower and stored. The cryoprecipitate-poor ("cryo-poor") plasma is immediately processed for capture (via, for example, primary chromatography) of labile coagulation factors such as factor IX complex and its components as well as protease inhibitors such as antithrombin and C1 esterase inhibitor. Serial centrifugation and precipitate isolation can be applied in subsequent steps. Such techniques are known to one of ordinary skill in the art and are described, for example, in U.S. Pat. Nos. 4,624,780, 5,219,995, 5,288,853, and U.S. patent application nos. 20140343255 and 20150343025, which disclosures are incorporated by reference in their entirety herein.

In an embodiment of the invention, the plasma fraction may comprise a plasma fraction containing a substantial concentration of albumin. In another embodiment of the invention, the plasma fraction may comprise a plasma fraction containing a substantial concentration of IgG or intravenous immune globulin (IGIV) (e.g. Gamunex-C®). In another embodiment of the invention the plasma fraction may comprise an IGIV plasma fraction, such as Gamunex-C® which has been substantially depleted of immune globulin (IgG) by methods well-known by one of ordinary skill in the art, such as for example, Protein A-mediated depletion. (See Keshishian, H., et al., *Multiplexed, Quantitative Workflow for Sensitive Biomarker Discovery in Plasma Yields Novel Candidates for Early Myocardial Injury*, Molecular & Cellular Proteomics, 14 at 2375-93 (2015)). In an additional embodiment, the blood plasma fraction may be one in which substantially all the clotting factors are removed in order to retain the efficacy of the fraction with reduced risk of thromboses. For example, the plasma fraction may be a plasma fraction as described in U.S. Patent No. 62/376,529 filed on Aug. 18, 2016; the disclosure of which is incorporated by reference in its entirety herein.

4. Albumin Products

To those having ordinary skill in the art, there are two general categories of Albumin Plasma Products ("APP"): plasma protein fraction (PPF) and human albumin solution (HAS). PPF is derived from a process with a higher yield than HAS, but has a lower minimum albumin purity than HAS (>83% for PPF and >95% for HAS). (*Production of human albumin solution: a continually developing colloid*, P. Matejtschuk et al., British J. of Anaesthesia 85(6): 887-95, at 888 (2000)). Additionally, some have noted that PPF has a disadvantage because of the presence of protein "contaminants" such as PKA. Id. As a consequence, PPF preparations have lost popularity as Albumin Plasma Products, and have even been delisted from certain countries' Pharmacopoeias. Id. Contrary to these concerns, the invention makes beneficial use of these "contaminants." Besides $\alpha$, $\beta$, and $\gamma$ globulins, as well as the aforementioned PKA, the methods of the invention utilize additional proteins or other factors within the "contaminants" that promote processes such as neurogenesis, neuronal cell survival, and improved cognition.

Those of skill in the art will recognize that there are, or have been, several commercial sources of PPF (the "Commercial PPF Preparations.") These include Plasma-Plex™ PPF (Armour Pharmaceutical Co., Tarrytown, N.Y.), Plasmanate™ PPF (Grifols, Clayton, N.C.), Plasmatein™ (Alpha Therapeutics, Los Angeles, Calif.), and Protenate™ PPF (Baxter Labs, Inc. Deerfield, Ill.).

Those of skill in the art will also recognize that there are, or have been, several commercial sources of HAS (the "Commercial HAS Preparations.") These include Albuminar™ (CSL Behring), AlbuRx™ (CSL Behring), Albutein™ (Grifols, Clayton, N.C.), Buminate™ (Baxatla, Inc., Bannockburn, Ill.), Flexbumin™ (Baxatla, Inc., Bannockburn, Ill.), and Plasbumin™ (Grifols, Clayton, N.C.).

A. Plasma Protein Fraction (Human) (PPF)

According to the United States Food and Drug Administration ("FDA"), "Plasma Protein Fraction (Human)," or PPF, is the proper name of the product defined as "a sterile solution of protein composed of albumin and globulin, derived from human plasma." (Code of Federal Regulations "CFR" 21 CFR 640.90 which is herein incorporated by reference). PPF's source material is plasma recovered from Whole Blood prepared as prescribed in 21 CFR 640.1-640.5 (incorporated by reference herein), or Source Plasma prepared as prescribed in 21 CFR 640.60-640.76 (incorporated by reference herein).

PPF is tested to determine it meets the following standards as per 21 CFR 640.92 (incorporated by reference herein):

(a) The final product shall be a 5.0+/−0.30 percent solution of protein; and (b) The total protein in the final product shall consist of at least 83 percent albumin, and no more than 17 percent globulins. No more than 1 percent of the total protein shall be gamma globulin. The protein composition is determined by a method that has been approved for each manufacturer by the Director, Center for Biologics Evaluation and Research, Food and Drug Administration.

As used herein, "Plasma Protein Fraction" or "PPF" refers to a sterile solution of protein composed of albumin and globulin, derived from human plasma, with an albumin content of at least 83% with no more than 17% globulins (including $\alpha 1$, $\alpha 2$, $\beta$, and $\gamma$ globulins) and other plasma proteins, and no more than 1% gamma globulin as determined by electrophoresis. (Hink, J. H., Jr., et al., Preparation and Properties of a Heat-Treated Human Plasma Protein Fraction, Vox Sanguinis 2(174) (1957)). PPF can also refer to a solid form, which when suspended in solvent, has similar composition. The total globulin fraction can be determined through subtracting the albumin from the total protein. (Busher, J., *Serum Albumin and Globulin*, Clinical Methods: The History, Physical, and Laboratory Examinations, Chapter 10, Walker H K, Hall W D, Hurst J D, eds. (1990)).

B. Albumin (Human) (HAS)

According to the FDA, "Albumin (Human)" (also referred to herein as "HAS") is the proper name of the product defined as "sterile solution of the albumin derived from human plasma." (Code of Federal Regulations "CFR" 21 CFR 640.80 which is herein incorporated by reference.) The source material for Albumin (Human) is plasma recovered from Whole Blood prepared as prescribed in 21 CFR 640.1-640.5 (incorporated by reference herein), or Source Plasma prepared as prescribed in 21 CFR 640.60-640.76 (incorporated by reference herein). Other requirements for Albumin (Human) are listed in 21 CFR 640.80-640.84 (incorporated by reference herein).

Albumin (Human) is tested to determine if it meets the following standards as per 21 CFR 640.82:

(a) Protein Concentration. Final product shall conform to one of the following concentrations: 4.0+/−0.25 percent; 5.0+/−0.30 percent; 20.0+/−1.2 percent; and 25.0+/−1.5 percent solution of protein.

(b) Protein Composition. At least 96 percent of the total protein in the final product shall be albumin, as determined by a method that has been approved for each manufacturer by the Director, Center for Biologics Evaluation and Research, Food and Drug Administration.

As used herein, "Albumin (Human)" or "HAS" refers to a to a sterile solution of protein composed of albumin and globulin, derived from human plasma, with an albumin content of at least 95%, with no more than 5% globulins (including α1, α2, β, and γ globulins) and other plasma proteins. HAS can also refer to a solid form, which when suspended in solvent, has similar composition. The total globulin fraction can be determined through subtracting the albumin from the total protein.

As can be recognized by one having ordinary skill in the art, PPF and HAS fractions can also be freeze-dried or in other solid form. Such preparations, with appropriate additives, can be used to make tablets, powders, granules, or capsules, for example. The solid form can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

5. Clotting Factor-Reduced Fractions

Another embodiment of the invention uses a blood plasma fraction from which substantially all of the clotting factors are removed in order to retain the efficacy of the fraction with reduced risk of thromboses. Conveniently, the blood product can be derived from a young donor or pool of young donors, and can be rendered devoid of IgM in order to provide a young blood product that is ABO compatible. Currently, plasma that is transfused is matched for ABO blood type, as the presence of naturally occurring antibodies to the A and B antigens can result in transfusion reactions. IgM appears to be responsible for transfusion reactions when patients are given plasma that is not ABO matched. Removal of IgM from blood products or fractions helps eliminate transfusion reactions in subjects who are administered the blood products and blood plasma fractions of the invention.

Accordingly, in one embodiment, the invention is directed to a method of treating or preventing an aging-related condition such as cognitive impairment or neurodegeneration in a subject. The method comprises: administering to the subject a blood product or blood fraction derived from whole-blood from an individual or pool of individuals, wherein the blood product or blood fraction is substantially devoid of (a) at least one clotting factor and/or (b) IgM. In some embodiments, the individual(s) from whom the blood product or blood fraction is derived are young individuals. In some embodiments, the blood product is substantially devoid of at least one clotting factor and IgM. In certain embodiments, the blood product is substantially devoid of fibrinogen (Factor I). In additional embodiments, the blood product substantially lacks erythrocytes and/or leukocytes. In further embodiments, the blood product is substantially acellular. In other embodiments, the blood product is derived from plasma. Such embodiments of the invention are further supported by U.S. Patent Application No. 62/376,529 filed on Aug. 18, 2016, which is incorporated by reference in its entirety herein.

6. Protein-Enriched Plasma Protein Products

Additional embodiments of the invention use plasma fractions with reduced albumin concentration compared to PPF, but with increased amounts of globulins and other plasma proteins (what have been referred to by some as "contaminants"). The embodiments, as with PPF, HAS, Effluent I, and Effluent II/III are all effectively devoid of clotting factors. Such plasma fractions are hereinafter referred to as "protein-enriched plasma protein products". For example, an embodiment of the invention may use a protein-enriched plasma protein product comprised of 82% albumin and 18% α, β, and γ globulins and other plasma proteins. Another embodiment of the invention may use a protein-enriched plasma protein product comprised of 81% albumin and 19% of α, β, and γ globulins and/or other plasma proteins. Another embodiment of the invention may use a protein-enriched plasma protein product comprised of 80% albumin and 20% of α, β, and γ globulins and/or other plasma proteins. Additional embodiments of the invention may use protein-enriched plasma protein products comprised of 70-79% albumin and a corresponding 21-30% of α, β, and γ globulins and other plasma proteins. Additional embodiments of the invention may use protein-enriched plasma protein products comprised of 60-69% albumin and a corresponding 31-40% of α, β, and γ globulins and other plasma proteins. Additional embodiments of the invention may use protein-enriched plasma protein products comprised of 50-59% albumin and a corresponding 41-50% of α, β, and γ globulins and other plasma proteins. Additional embodiments of the invention may use protein-enriched plasma protein products comprised of 40-49% albumin and a corresponding 51-60% of α, β, and γ globulins and other plasma proteins. Additional embodiments of the invention may use protein-enriched plasma protein products comprised of 30-39% albumin and a corresponding 61-70% of α, β, and γ globulins and other plasma proteins. Additional embodiments of the invention may use protein-enriched plasma protein products comprised of 20-29% albumin and a corresponding 71-80% of α, β, and γ globulins and other plasma proteins. Additional embodiments of the invention may use protein-enriched plasma protein products comprised of 10-19% albumin and a corresponding 81-90% of α, β, and γ globulins and other plasma proteins. Additional embodiments of the invention may use protein-enriched plasma protein products comprised of 1-9% albumin and a corresponding 91-99% of α, β, and γ globulins and other plasma proteins. A further embodiment of the invention may use protein-enriched plasma protein products comprised of 0-1% albumin and 99-100% of α, β, and γ globulins and other plasma proteins Embodiments of the invention described above may also have total gamma globulin concentrations of 0-5%.

The specific concentrations of proteins in a plasma fraction may be determined using techniques well-known to a person having ordinary skill in the relevant art. By way of example, and not limitation, such techniques include electrophoresis, mass spectrometry, ELISA analysis, and Western blot analysis.

7. Preparation of Blood Plasma Fractions

Methods of preparing PPF and other plasma fractions are well-known to those having ordinary skill in the art. An embodiment of the invention allows for blood used in the preparation of human plasma protein fraction to be collected in flasks with citrate or anticoagulant citrate dextrose solution for inhibition of coagulation, with further separation of Fractions I, II+III, IV, and PPF as per the method disclosed in Hink et al. (See Hink, J. H., Jr., et al., Preparation and Properties of a Heat-Treated Human Plasma Protein Fraction, VOX SANGUINIS 2(174) (1957), herein incorporated by reference.) According to this method, the mixture can be collected to 2-8° C. The plasma can then subsequently be separated by centrifugation at 7° C., removed, and stored at −20° C. The plasma can then be thawed at 37° C. and fractionated, preferably within eight hours after removal from −20° C. storage.

Plasma can be separated from Fraction I using 8% ethanol at pH 7.2 and a temperature at −2 to −2.5° C. with protein concentration of 5.1 to 5.6 percent. Cold 53.3 percent ethanol (176 mL/L of plasma) with acetate buffer (200 mL 4M sodium acetate, 230 mL glacial acetic acid quantum satis to 1 L with $H_2O$) can be added using jets at a rate, for example, of 450 mL/minute during the lowering the plasma temperature to −2° C. Fraction I can be separated and removed from the effluent (Effluent I) through ultracentrifugation. Fibrinogen can be obtained from Fraction I as per methods well-known to those having ordinary skill in the art.

Fraction II+III can be separated from Effluent I through adjustment of the effluent to 21 percent ethanol at pH 6.8, temperature at −6° C., with protein concentration of 4.3 percent. Cold 95 percent ethanol (176 mL/L of Effluent I) with 10 M acetic acid used for pH adjustment can be added using jets at a rate, for example, of 500 mL/minute during the lowering of the temperature of Effluent I to −6° C. The resulting precipitate (Fraction II+III) can be removed by centrifugation at −6° C. Gamma globulin can be obtained from Fraction II+III using methods well-known to those having ordinary skill in the art.

Fraction IV-1 can be separated from Effluent II+III ("Effluent II/III") through adjustment of the effluent to 19 percent ethanol at pH 5.2, temperature at −6° C., and protein concentration of 3 percent. $H_2O$ and 10 M acetic acid used for pH adjustment can be added using jets while maintaining Effluent II/III at −6° C. for 6 hours. Precipitated Fraction VI-1 can be settled at −6° C. for 6 hours and subsequently separated from the effluent by centrifugation at the same temperature. Stable plasma protein fraction can be recovered from Effluent IV-1 through adjustment of the ethanol concentration to 30 percent at pH 4.65, temperature −7° C. and protein concentration of 2.5 percent. This can be accomplished by adjusting the pH of Effluent IV-1 with cold acid-alcohol (two parts 2 M acetic acid and one part 95 percent ethanol). While maintaining a temperature of −7° C., to every liter of adjusted Effluent IV-1 170 mL cold ethanol (95%) is added. Proteins that precipitate can be allowed to settle for 36 hours and subsequently removed by centrifugation at −7° C.

The recovered proteins (stable plasma protein fraction) can be dried (e.g. by freeze drying) to remove alcohol and $H_2O$. The resulting dried powder can be dissolved in sterile distilled water, for example using 15 liters of water/kg of powder, with the solution adjusted to pH 7.0 with 1 M NaOH. A final concentration of 5 percent protein can be achieved by adding sterile distilled water containing sodium acetyl tryptophanate, sodium caprylate, and NaCl, adjusting to final concentrations of 0.004 M acetyl tryptophanate, 0.004 M caprylate, and 0.112 M sodium. Finally, the solution can be filtered at 10° C. to obtain a clear solution and subsequently heat-treated for inactivation of pathogens at 60° C. for at least 10 hours.

One having ordinary skill in the art would recognize that each of the different fractions and effluents described above could be used with the methods of the invention to treat disease. For example, and not by way of limitation, Effluents I or Effluent II/III may be utilized to treat such diseases as cognitive and neurodegenerative disorders and are embodiments of the invention.

The preceding methods of preparing blood plasma fractions and plasma protein fraction (PPF) are only exemplary and involves merely embodiments of the invention. One having ordinary skill in the art would recognize that these methods can vary. For example, pH, temperature, and ethanol concentration, among other things can be adjusted to produce different variations of plasma fractions and plasma protein fraction in the different embodiments and methods of the invention. In another example, additional embodiments of the invention contemplate the use of nanofiltration for the removal/inactivation of pathogens from plasma fractions and plasma protein fraction.

An additional embodiment of the invention contemplates methods and composition using and/or comprising additional blood plasma fractions. For example, the invention, among other things, demonstrates that specific concentrations of albumin are not critical for improving cognitive activity. Hence, fractions with reduced albumin concentration, such as those fractions having below 83% albumin, are contemplated by the invention.

8. Treatment

Aspects of the methods of the inventions described herein include treatment of a subject with a plasma comprising blood product, such as a blood plasma fraction, e.g., as described above. An embodiment includes treatment of a human subject with a plasma comprising blood product. One of skill in the art would recognize that methods of treatment of subjects with plasma comprising blood products are recognized in the art. By way of example, and not limitation, one embodiment of the methods of the inventions described herein is comprised of administering fresh frozen plasma to a subject for treatment and/or prevention of cognitive impairment and/or age-related dementia. In one embodiment, the plasma comprising blood product is administered immediately, e.g., within about 12-48 hours of collection from a donor, to the individual suffering or at risk from a cognitive impairment and/or age-related dementia. In such instances, the product may be stored under refrigeration, e.g., 0-10° C. In another embodiment, fresh frozen plasma is one that has been stored frozen (cryopreserved) at −18° C. or colder. Prior to administration, the fresh frozen plasma is thawed and once thawed, administered to a subject 60-75 minutes after the thawing process has begun. Each subject preferably receives a single unit of fresh frozen plasma (200-250 mL), the fresh frozen plasma preferably derived from donors of a pre-determined age range. In one embodiment of the invention, the fresh frozen plasma is donated by (derived from) young individuals. In another embodiment of the invention, the fresh frozen plasma is donated by (derived from) donors of the same gender. In another embodiment of the invention, the fresh frozen plasma is donated by (derived from) donors of the age range between 18-22 years old. In one embodiment, subjects are treated twice per week with 3-4 days between infusions. In an embodiment of the invention, treatment persists until a specific endpoint is reached.

In an embodiment of the invention, the plasma comprising blood products are screened after donation by blood type. In another embodiment of the invention, the plasma comprising blood products are screened for infectious disease agents such as HIV I & II, HBV, HCV, HTLV I & II, anti-HBc per the requirements of 21 CFR 640.33 and recommendations contained in FDA guidance documents.

In yet another embodiment of the invention, the subject is treated with a "Plasma Fraction." In an embodiment of the invention, the Plasma Fraction is PPF or HAS. In a further embodiment of the invention, the Plasma Fraction is one of the Commercial PPF Preparations of the Commercial HAS Preparations. In another embodiment of the invention the Plasma Fraction is a PPF or HAS derived from a pool of individuals of a specific age range, such as young individuals, or is a modified PPF or HAS fraction which has been subjected to additional fractionation or processing (e.g. PPF or HAS with one or more specific proteins partially or substantially removed). In another embodiment of the invention, the Plasma Fraction is an IGIV plasma fraction which has been substantially depleted of immune globulin (IgG). A blood fraction which is "substantially depleted" or which has specific proteins "substantially removed," such as IgG, refers to a blood fraction containing less than about 50% of the amount that occurs in the reference product or whole blood plasma, such as less than 45%, 40%, 35%, 30%, 25%, 20%, 15%, 5%, 4%, 3%, 2%, 1%, 0.5%, 0.25%, 0.1%, undetectable levels, or any integer between these values, as measured using standard assays well known in the art.

9. Monitoring

Another aspect of the present invention relates to methods of monitoring the effect of a medication on a subject for treating cognitive impairment and/or age-related dementia, the method comprising comparing cognitive function before and after treatment. Those having ordinary skill in the art recognize that there are well-known methods of evaluating cognitive function. For example, and not by way of limitation, the method may comprise evaluation of cognitive function based on medical history, family history, physical and neurological examinations by clinicians who specialize dementia and cognitive function, laboratory tests, and neuropsychological assessment. Additional embodiments which are contemplated by the invention include: the assessment of consciousness, such as using the Glasgow Coma Scale (EMV); mental status examination, including the abbreviated mental test score (AMTS) or mini-mental state examination (MMSE) (Folstein et al., J. Psychiatr. Res 1975; 12:1289-198); global assessment of higher functions; estimation of intracranial pressure such as by fundoscopy.

In one embodiment, examinations of peripheral nervous system may be used to evaluate cognitive function, including any one of the followings: sense of smell, visual fields and acuity, eye movements and pupils (sympathetic and parasympathetic), sensory function of face, strength of facial and shoulder girdle muscles, hearing, taste, pharyngeal movement and reflex, tongue movements, which can be tested individually (e.g. the visual acuity can be tested by a Snellen chart; a reflex hammer used testing reflexes including masseter, biceps and triceps tendon, knee tendon, ankle jerk and plantar (i.e. Babinski sign); Muscle strength often on the MRC scale 1 to 5; Muscle tone and signs of rigidity.

10. Administration

In practicing methods of the invention, a blood plasma fraction is administered to the subject. In an embodiment, the blood plasma fraction is administered by intravenous infusion. The rate of infusion may vary, but in one embodiment of the invention, the infusion rate is 5-8 mL/minute. Those having ordinary skill in the art will recognize that the infusion rate can depend upon the subject's condition and response to administration.

In those embodiments where an effective amount of an active agent is administered to the adult mammal, the amount or dosage is effective when administered for a suitable period of time, such as one week or longer, including two weeks or longer, such as 3 weeks or longer, one month or longer, 2 months or longer, 3 months or longer, 4 months or longer, 5 months or longer, 6 months or longer, 1 year or longer etc., so as to evidence a reduction in the condition, e.g., cognitive impairment, or delay of cognitive impairment and/or cognitive improvement in the adult mammal. For example, an effective dose is the dose that, when administered for a suitable period of time, will slow e.g., by about 20% or more, e.g., by 30% or more, by 40% or more, or by 50% or more, in some instances by 60% or more, by 70% or more, by 80% or more, or by 90% or more. For example, will halt, cognitive decline in a patient suffering from natural aging or an aging-associated disorder. In some instances, an effective amount or dose of blood product will not only slow or halt the progression of the disease condition but will also induce the reversal of the condition, i.e., will cause an improvement in cognitive ability. For example, in some instances, an effective amount is the amount that when administered for a suitable period of time, usually at least about one week, and maybe about two weeks, or more, up to a person of about 3 weeks, 4 weeks, 8 weeks, or longer will improve the cognitive abilities of an individual suffering from an aging-associated cognitive impairment by, for example, 1.5-fold, 2-fold, 3-fold, 4-fold, 5-fold, in some instances 6-fold, 7-fold, 8-fold, 9-fold, or 10-fold or more relative to cognition prior to administration of the blood product or fraction. In some instances, an effective amount or dose of active agent will not only slow or halt the progression of the disease condition but will also induce the reversal of the condition, i.e., will cause an improvement in cognitive function. For example, in some instances, an effective amount is the amount that when administered for a suitable period of time, will improve the symptoms an individual suffering from cognitive decline or impairment, for example 1.5-fold, 2-fold, 3-fold, 4-fold, 5-fold, in some instances 6-fold, 7-fold, 8-fold, 9-fold, or 10-fold or more relative to untreated individuals prior to administration of the agent.

In other embodiments, the blood plasma fraction or Plasma Fraction is administered in accordance with one or more dosing regimens described in U.S. Patent Application No. 62/490,519, which is herein incorporated by reference in its entirety. As such, an embodiment of the invention includes treating a subject diagnosed with a cognitive impairment by administering to the subject an effective amount of blood plasma or Plasma Fraction wherein the blood plasma or Plasma Fraction is administered in a manner resulting in improved cognitive function or neurogenesis after the mean or median half-life of the blood plasma proteins or Plasma Fraction proteins been reached, relative to the most recent administered dose (referred to as "Pulsed Dosing" or "Pulse Dosed" herein). Another embodiment of the invention includes administering the blood plasma or Plasma Fraction via a dosing regimen of at least two consecutive days and monitoring the subject for improved cognitive function at least 3 days after the date of last administration. A further embodiment of the invention includes administering the blood plasma or Plasma Fraction via a dosing regimen of at least 3, 4, 5, 6, 7, 8, 9, 10, 11, 12, 13, or 14 consecutive days and monitoring the subject for improved cognitive function at least 3 days after the date of last administration. Yet another embodiment of the invention includes administering the blood plasma or Plasma Fraction via a dosing regimen of at least 2 consecutive days and after the date of last administration, monitoring for cognitive improvement beyond when the average half-life of the proteins in the blood plasma or Plasma Fraction has been reached. Another embodiment of the invention includes administering the blood plasma or Plasma Fraction via a dosing regimen of 2 to 14 non-consecutive days wherein each gap between doses may be between 0-3 days each. In some instances, Pulsed Dosing in accordance with the invention includes administration of a first set of doses, e.g., as described above, followed by a period of no dosing, e.g., a "dosing-free period", which in turn is followed by administration of another dose or set of doses. The duration of this "dosing-free" period, may vary, but in some embodiments, is 7 days or longer, such as 10 days or longer, including 14 days or longer, wherein some instances the dosing-free period ranges from 15 to 365 days, such as 30 to 90 days and including 30 to 60 days. As such, embodiments of the methods include non-chronic (i.e., non-continuous) dosing, e.g., non-chronic administration of a blood plasma product. In some embodiments, the pattern of Pulsed Dosing followed by a dosing-free period is repeated for a number of times, as desired, where in some instances this pattern is continued for 1 year or longer, such as 2 years or longer, up to and including the life of the subject. Another embodiment of the invention includes administering the blood plasma or Plasma Fraction via a dosing regimen of 5 consecutive days, with a dosing-free period of 2-3 days, followed by administration for 2-14 consecutive days.

Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances, reverse the progression of the cognitive impairment or age-associated dementia.

11. Plasma Protein Fraction

In practicing methods of the invention, a plasma fraction is administered to the subject. In an embodiment, the Plasma Fraction is plasma protein fraction (PPF). In additional embodiments, the PPF is selected from the Commercial PPF Preparations.

In another embodiment, the PPF is comprised of 88% normal human albumin, 12% alpha and beta globulins and not more than 1% gamma globulin as determined by electrophoresis. Embodiments of this embodiment used in practicing methods of the invention include, for example, this embodiment as a 5% solution of PPF buffered with sodium carbonate and stabilized with 0.004 M sodium caprylate and 0.004 M acetyltryptophan. Additional formulations, including those modifying the percentage of PPF (e.g. about 1% to about 10%, about 10% to about 20%, about 20% to 25%, about 25% to 30%) in solution as well as the concentrations of solvent and stabilizers may be utilized in practicing methods of the invention.

12. Plasma Fractions of Specific Donor Age

An embodiment of invention includes administering a blood plasma fraction or a Plasma Fraction derived from the plasma of individuals of certain age ranges. Additional embodiments include administering a plasma protein fraction derived from the plasma of individuals of certain age ranges. An embodiment includes administering a PPF or a HAS which has been derived from the plasma of young individuals. In another embodiment of the invention the young individuals are of a single specific age or a specific age range. In yet another embodiment, the average age of the donors is less than that of the subject or less than the average age of the subjects being treated.

Certain embodiments of the invention include pooling blood or blood plasma from individuals of specific age ranges and fractionating the blood plasma as described above to attain a plasma protein fraction product such as PPF or HAS. In an alternate embodiment of the invention, the plasma protein fraction or specific plasma protein fraction is attained from specific individuals fitting a specified age range. In another embodiment of the invention, the blood plasma fraction, Plasma Fraction, or specific plasma protein fraction product is attained from a pool of young individuals, of which "young" may be determined by chronologic or biologic age as described above, and the age(s) of the individuals may be a specific age or age range.

13. Indications

The subject methods and plasma-comprising blood products and fractions find use in treating, including preventing, aging-associated conditions, such as impairments in the cognitive ability of individuals, e.g., cognitive disorders, including (but not limited to) age-associated dementia, immunological conditions, cancer, and physical and functional decline. Individuals suffering from or at risk of developing an aging-associated cognitive impairment that will benefit from treatment with the subject plasma-comprising blood product, e.g., by the methods disclosed herein, include individuals that are about 50 years old or older, e.g., 60 years old or older, 70 years old or older, 80 years old or older, 90 years old or older, and 100 years old or older, i.e., between the age of about 50 and 100, e.g., 50, 55, 60, 65, 70, 75, 80, 85, 90, 95 or about 100 years old, and are suffering from cognitive impairment associated with natural aging process, e.g., mild cognitive impairment (M.C.I.); and individuals that are about 50 years old or older, e.g., 60 years old or older, 70 years old or older, 80 years old or older, 90 years old or older, and usually no older than 100 years old, i.e., between the ages of about 50 and 90, e.g., 50, 55, 60, 65, 70, 75, 80, 85, 90, 95 or about 100 years old, that have not yet begun to show symptoms of cognitive impairment. Examples of cognitive impairments that are due to natural aging include the following:

A. Mild cognitive impairment (M.C.I.) is a modest disruption of cognition that manifests as problems with memory or other mental functions such as planning, following instructions, or making decisions that have worsened over time while overall mental function and daily activities are not impaired. Thus, although significant neuronal death does not typically occur, neurons in the aging brain are vulnerable to sub-lethal age-related alterations in structure, synaptic integrity, and molecular processing at the synapse, all of which impair cognitive function.

Individuals suffering from or at risk of developing an aging-associated cognitive impairment that will benefit from treatment with the subject plasma-comprising blood product or fraction, e.g., by the methods disclosed herein, also include individuals of any age that are suffering from a cognitive impairment due to an aging-associated disorder; and individuals of any age that have been diagnosed with an aging-associated disorder that is typically accompanied by cognitive impairment, where the individual has not yet begun to present with symptoms of cognitive impairment. Examples of such aging-associated disorders include the following:

B. Alzheimer's disease. Alzheimer's disease is a progressive, inexorable loss of cognitive function associated with an excessive number of senile plaques in the cerebral cortex and subcortical gray matter, which also contains b-amyloid and neurofibrillary tangles consisting of tau protein. The common form affects persons>60 yr old, and its incidence increases as age advances. It accounts for more than 65% of the dementias in the elderly.

The cause of Alzheimer's disease is not known. The disease runs in families in about 15 to 20% of cases. The remaining, so-called sporadic cases have some genetic determinants. The disease has an autosomal dominant genetic pattern in most early-onset and some late-onset cases but a variable late-life penetrance. Environmental factors are the focus of active investigation.

In the course of the disease, synapses, and ultimately neurons are lost within the cerebral cortex, hippocampus, and subcortical structures (including selective cell loss in the nucleus basalis of Meynert), locus coeruleus, and nucleus raphae dorsalis. Cerebral glucose use and perfusion is reduced in some areas of the brain (parietal lobe and temporal cortices in early-stage disease, prefrontal cortex in late-stage disease). Neuritic or senile plaques (composed of neurites, astrocytes, and glial cells around an amyloid core) and neurofibrillary tangles (composed of paired helical filaments) play a role in the pathogenesis of Alzheimer's disease. Senile plaques and neurofibrillary tangles occur with normal aging, but they are much more prevalent in persons with Alzheimer's disease.

C. Parkinson's Disease. Parkinson's Disease (PD) is an idiopathic, slowly progressive, degenerative CNS disorder characterized by slow and decreased movement, muscular rigidity, resting tremor, and postural instability. Originally considered primarily a motor disorder, PD is now recognized to also affect cognition, behavior, sleep, autonomic function, and sensory function. The most common cognitive impairments include an impairment in attention and concentration, working memory, executive function, producing language, and visuospatial function.

In primary Parkinson's disease, the pigmented neurons of the substantia nigra, locus coeruleus, and other brain stem dopaminergic cell groups are lost. The cause is not known. The loss of substantia nigra neurons, which project to the caudate nucleus and putamen, results in depletion of the neurotransmitter dopamine in these areas. Onset is generally after age 40, with increasing incidence in older age groups.

Secondary parkinsonism results from loss of or interference with the action of dopamine in the basal ganglia due to other idiopathic degenerative diseases, drugs, or exogenous toxins. The most common cause of secondary parkinsonism is ingestion of antipsychotic drugs or reserpine, which produce parkinsonism by blocking dopamine receptors. Less common causes include carbon monoxide or manganese poisoning, hydrocephalus, structural lesions (tumors, infarcts affecting the midbrain or basal ganglia), subdural hematoma, and degenerative disorders, including striatonigral degeneration.

D. Frontotemporal dementia. Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. Symptoms are classified into three groups based on the functions of the frontal and temporal lobes affected:

Behavioral variant FTD (bvFTD), with symptoms include lethargy and aspontaneity on the one hand, and disinhibition on the other; progressive nonfluent aphasia (PNFA), in which a breakdown in speech fluency due to articulation difficulty, phonological and/or syntactic errors is observed but word comprehension is preserved; and semantic dementia (SD), in which patients remain fluent with normal phonology and syntax but have increasing difficulty with naming and word comprehension. Other cognitive symptoms common to all FTD patients include an impairment in executive function and ability to focus. Other cognitive abilities, including perception, spatial skills, memory and praxis typically remain intact. FTD can be diagnosed by observation of reveal frontal lobe and/or anterior temporal lobe atrophy in structural MRI scans.

A number of forms of FTD exist, any of which may be treated or prevented using the subject methods and compositions. For example, one form of frontotemporal dementia is Semantic Dementia (SD). SD is characterized by a loss of semantic memory in both the verbal and non-verbal domains. SD patients often present with the complaint of word-finding difficulties. Clinical signs include fluent aphasia, anomia, impaired comprehension of word meaning, and associative visual agnosia (the inability to match semantically related pictures or objects). As the disease progresses, behavioral and personality changes are often seen similar to those seen in frontotemporal dementia although cases have been described of 'pure' semantic dementia with few late behavioral symptoms. Structural MRI imaging shows a characteristic pattern of atrophy in the temporal lobes (predominantly on the left), with inferior greater than superior involvement and anterior temporal lobe atrophy greater than posterior.

As another example, another form of frontotemporal dementia is Pick's disease (PiD, also PcD). A defining characteristic of the disease is build-up of tau proteins in neurons, accumulating into silver-staining, spherical aggregations known as "Pick bodies." Symptoms include loss of speech (aphasia) and dementia. Patients with orbitofrontal dysfunction can become aggressive and socially inappropriate. They may steal or demonstrate obsessive or repetitive stereotyped behaviors. Patients with dorsomedial or dorsolateral frontal dysfunction may demonstrate a lack of concern, apathy, or decreased spontaneity. Patients can demonstrate an absence of self-monitoring, abnormal self-awareness, and an inability to appreciate meaning. Patients with gray matter loss in the bilateral posterolateral orbitofrontal cortex and right anterior insula may demonstrate changes in eating behaviors, such as a pathologic sweet tooth. Patients with more focal gray matter loss in the anterolateral orbitofrontal cortex may develop hyperphagia. While some of the symptoms can initially be alleviated, the disease progresses and patients often die within two to ten years.

E. Huntington's disease. Huntington's disease (HD) is a hereditary progressive neurodegenerative disorder characterized by the development of emotional, behavioral, and psychiatric abnormalities; loss of intellectual or cognitive functioning; and movement abnormalities (motor disturbances). The classic signs of HD include the development of chorea—involuntary, rapid, irregular, jerky movements that may affect the face, arms, legs, or trunk—as well as cognitive decline including the gradual loss of thought processing and acquired intellectual abilities. There may be impairment of memory, abstract thinking, and judgment; improper perceptions of time, place, or identity (disorientation); increased agitation; and personality changes (personality disintegration). Although symptoms typically become evident during the fourth or fifth decades of life, the age at onset is variable and ranges from early childhood to late adulthood (e.g., 70s or 80s).

HD is transmitted within families as an autosomal dominant trait. The disorder occurs as the result of abnormally long sequences or "repeats" of coded instructions within a gene on chromosome 4 (4p16.3). The progressive loss of nervous system function associated with HD results from loss of neurons in certain areas of the brain, including the basal ganglia and cerebral cortex.

F. Amyotrophic lateral sclerosis. Amyotrophic lateral sclerosis (ALS) is a rapidly progressive, invariably fatal, neurological disease that attacks motor neurons. Muscular weakness and atrophy and signs of anterior horn cell dysfunction are initially noted most often in the hands and less often in the feet. The site of onset is random, and progression is asymmetric. Cramps are common and may precede weakness. Rarely, a patient survives 30 years; 50% die within 3 years of onset, 20% live 5 years, and 10% live 10 years.

Diagnostic features include onset during middle or late adult life and progressive, generalized motor involvement without sensory abnormalities. Nerve conduction velocities are normal until late in the disease. Recent studies have documented the presentation of cognitive impairments as well, particularly a reduction in immediate verbal memory, visual memory, language, and executive function.

A decrease in cell body area, number of synapses and total synaptic length has been reported in even normal-appearing neurons of the ALS patients. It has been suggested that when the plasticity of the active zone reaches its limit, a continuing loss of synapses can lead to functional impairment. Promoting the formation or new synapses or preventing synapse loss may maintain neuron function in these patients.

G. Multiple Sclerosis. Multiple Sclerosis (MS) is characterized by various symptoms and signs of CNS dysfunction, with remissions and recurring exacerbations. The most common presenting symptoms are paresthesias in one or more extremities, in the trunk, or on one side of the face; weakness or clumsiness of a leg or hand; or visual disturbances, e.g., partial blindness and pain in one eye (retrobulbar optic neuritis), dimness of vision, or scotomas. Common cognitive impairments include impairments in memory (acquiring, retaining, and retrieving new information), attention and concentration (particularly divided attention), information processing, executive functions, visuospatial functions, and verbal fluency. Common early symptoms are ocular palsy resulting in double vision (diplopia), transient weakness of one or more extremities, slight stiffness or unusual fatigability of a limb, minor gait disturbances, difficulty with bladder control, vertigo, and mild emotional disturbances; all indicate scattered CNS involvement and often occur months or years before the disease is recognized. Excess heat may accentuate symptoms and signs.

The course is highly varied, unpredictable, and, in most patients, remittent. At first, months or years of remission may separate episodes, especially when the disease begins with retrobulbar optic neuritis. However, some patients have frequent attacks and are rapidly incapacitated; for a few the course can be rapidly progressive.

H. Glaucoma. Glaucoma is a common neurodegenerative disease that affects retinal ganglion cells (RGCs). Evidence supports the existence of compartmentalized degeneration programs in synapses and dendrites, including in RGCs. Recent evidence also indicates a correlation between cognitive impairment in older adults and glaucoma (Yochim B P, et al. Prevalence of cognitive impairment, depression, and anxiety symptoms among older adults with glaucoma. J Glaucoma. 2012; 21(4):250-254).

I. Myotonic dystrophy. Myotonic dystrophy (DM) is an autosomal dominant multisystem disorder characterized by dystrophic muscle weakness and myotonia. The molecular defect is an expanded trinucleotide (CTG) repeat in the 3' untranslated region of the myotoninprotein kinase gene on chromosome 19q. Symptoms can occur at any age, and the range of clinical severity is broad. Myotonia is prominent in the hand muscles, and ptosis is common even in mild cases. In severe cases, marked peripheral muscular weakness occurs, often with cataracts, premature balding, hatchet facies, cardiac arrhythmias, testicular atrophy, and endocrine abnormalities (e.g., diabetes mellitus). Mental retardation is common in severe congenital forms, while an aging-related decline of frontal and temporal cognitive functions, particularly language and executive functions, is observed in milder adult forms of the disorder. Severely affected persons die by their early 50s.

J. Dementia. Dementia describes a class of disorders having symptoms affecting thinking and social abilities severely enough to interfere with daily functioning. Other instances of dementia in addition to the dementia observed in later stages of the aging-associated disorders discussed above include vascular dementia, and dementia with Lewy bodies, described below.

In vascular dementia, or "multi-infarct dementia", cognitive impairment is caused by problems in supply of blood to the brain, typically by a series of minor strokes, or sometimes, one large stroke preceded or followed by other smaller strokes. Vascular lesions can be the result of diffuse cerebrovascular disease, such as small vessel disease, or focal lesions, or both. Patients suffering from vascular dementia present with cognitive impairment, acutely or subacutely, after an acute cerebrovascular event, after which progressive cognitive decline is observed. Cognitive impairments are similar to those observed in Alzheimer's disease, including impairments in language, memory, complex visual processing, or executive function, although the related changes in the brain are not due to AD pathology but to chronic reduced blood flow in the brain, eventually resulting in dementia. Single photon emission computed tomography (SPECT) and positron emission tomography (PET) neuroimaging may be used to confirm a diagnosis of multi-infarct dementia in conjunction with evaluations involving mental status examination.

Dementia with Lewy bodies (DLB, also known under a variety of other names including Lewy body dementia, diffuse Lewy body disease, cortical Lewy body disease, and senile dementia of Lewy type) is a type of dementia characterized anatomically by the presence of Lewy bodies (clumps of alpha-synuclein and ubiquitin protein) in neurons, detectable in post mortem brain histology. Its primary feature is cognitive decline, particularly of executive functioning. Alertness and short term memory will rise and fall.

Persistent or recurring visual hallucinations with vivid and detailed pictures are often an early diagnostic symptom. DLB it is often confused in its early stages with Alzheimer's disease and/or vascular dementia, although, where Alzheimer's disease usually begins quite gradually, DLB often has a rapid or acute onset. DLB symptoms also include motor symptoms similar to those of Parkinson's. DLB is distinguished from the dementia that sometimes occurs in Parkinson's disease by the time frame in which dementia symptoms appear relative to Parkinson symptoms. Parkinson's disease with dementia (POD) would be the diagnosis when dementia onset is more than a year after the onset of Parkinson's. DLB is diagnosed when cognitive symptoms begin at the same time or within a year of Parkinson symptoms.

K. Progressive supranuclear palsy. Progressive supranuclear palsy (PSP) is a brain disorder that causes serious and progressive problems with control of gait and balance, along with complex eye movement and thinking problems. One of the classic signs of the disease is an inability to aim the eyes properly, which occurs because of lesions in the area of the brain that coordinates eye movements. Some individuals describe this effect as a blurring. Affected individuals often show alterations of mood and behavior, including depression and apathy as well as progressive mild dementia. The disorder's long name indicates that the disease begins slowly and continues to get worse (progressive), and causes weakness (palsy) by damaging certain parts of the brain above pea-sized structures called nuclei that control eye movements (supranuclear). PSP was first described as a distinct disorder in 1964, when three scientists published a paper that distinguished the condition from Parkinson's disease. It is sometimes referred to as Steele-Richardson-Olszewski syndrome, reflecting the combined names of the scientists who defined the disorder. Although PSP gets progressively worse, no one dies from PSP itself.

L. Ataxia. People with ataxia have problems with coordination because parts of the nervous system that control movement and balance are affected. Ataxia may affect the fingers, hands, arms, legs, body, speech, and eye movements. The word ataxia is often used to describe a symptom of incoordination which can be associated with infections, injuries, other diseases, or degenerative changes in the central nervous system. Ataxia is also used to denote a group of specific degenerative diseases of the nervous system called the hereditary and sporadic ataxias which are the National Ataxia Foundation's primary emphases.

M. Multiple-system atrophy. Multiple-system atrophy (MSA) is a degenerative neurological disorder. MSA is associated with the degeneration of nerve cells in specific areas of the brain. This cell degeneration causes problems with movement, balance, and other autonomic functions of the body such as bladder control or blood-pressure regulation.

The cause of MSA is unknown and no specific risk factors have been identified. Around 55% of cases occur in men, with typical age of onset in the late 50s to early 60s. MSA often presents with some of the same symptoms as Parkinson's disease. However, MSA patients generally show minimal if any response to the dopamine medications used for Parkinson's.

N. Frailty. Frailty Syndrome ("Frailty") is a geriatric syndrome characterized by functional and physical decline including decreased mobility, muscle weakness, physical slowness, poor endurance, low physical activity, malnourishment, and involuntary weight loss. Such decline is often accompanied and a consequence of diseases such as cognitive dysfunction and cancer. However, Frailty can occur even without disease. Individuals suffering from Frailty have an increased risk of negative prognosis from fractures, accidental falls, disability, comorbidity, and premature mortality. (C. Buigues, et al. Effect of a Prebiotic Formulation on Frailty Syndrome: A Randomized, Double-Blind Clinical Trial, Int. J. Mol. Sci. 2016, 17, 932). Additionally, individuals suffering from Frailty have an increased incidence of higher health care expenditure. (Id.)

Common symptoms of Frailty can be determined by certain types of tests. For example, unintentional weight loss involves a loss of at least 10 lbs. or greater than 5% of body weight in the preceding year; muscle weakness can be determined by reduced grip strength in the lowest 20% at baseline (adjusted for gender and BMI); physical slowness can be based on the time needed to walk a distance of 15 feet; poor endurance can be determined by the individual's self-reporting of exhaustion; and low physical activity can be measured using a standardized questionnaire. (Z. Palace et al., The Frailty Syndrome, Today's Geriatric Medicine 7(1), at 18 (2014)).

In some embodiments, the subject methods and compositions find use in slowing the progression of aging-associated cognitive impairment. In other words, cognitive abilities in the individual will decline more slowly following treatment by the disclosed methods than prior to or in the absence of treatment by the disclosed methods. In some such instances, the subject methods of treatment include measuring the progression of cognitive decline after treatment, and determining that the progression of cognitive decline is reduced. In some such instances, the determination is made by comparing to a reference, e.g., the rate of cognitive decline in the individual prior to treatment, e.g., as determined by measuring cognition prior at two or more time points prior to administration of the subject blood product.

The subject methods and compositions also find use in stabilizing the cognitive abilities of an individual, e.g., an individual suffering from aging-associated cognitive decline or an individual at risk of suffering from aging-associated cognitive decline. For example, the individual may demonstrate some aging-associated cognitive impairment, and progression of cognitive impairment observed prior to treatment with the disclosed methods will be halted following treatment by the disclosed methods. As another example, the individual may be at risk for developing an aging-associated cognitive decline (e.g., the individual may be aged 50 years old or older, or may have been diagnosed with an aging-associated disorder), and the cognitive abilities of the individual are substantially unchanged, i.e., no cognitive decline can be detected, following treatment by the disclosed methods as compared to prior to treatment with the disclosed methods.

The subject methods and compositions also find use in reducing cognitive impairment in an individual suffering from an aging-associated cognitive impairment. In other words, cognitive ability is improved in the individual following treatment by the subject methods. For example, the cognitive ability in the individual is increased, e.g., by 2-fold or more, 5-fold or more, 10-fold or more, 15-fold or more, 20-fold or more, 30-fold or more, or 40-fold or more, including 50-fold or more, 60-fold or more, 70-fold or more, 80-fold or more, 90-fold or more, or 100-fold or more, following treatment by the subject methods relative to the cognitive ability that is observed in the individual prior to treatment by the subject methods. In some instances, treatment by the subject methods and compositions restores the cognitive ability in the individual suffering from aging-associated cognitive decline, e.g., to their level when the individual was about 40 years old or less. In other words, cognitive impairment is abrogated.

14. Methods of Diagnosing and Monitoring for Improvement of Neurocognitive-Associated Disease In some instances, among the variety of methods to diagnose and monitor disease progression and improvement in neurocognitive-associated disease, the following types of assessments are used alone or in combination with subjects suffering from neurodegenerative disease, as desired. The following types of methods are presented as examples and are not limited to the recited methods. Any convenient methods to monitor disease may be used in practicing the invention, as desired. Those methods are also contemplated by the methods of the invention.

A. General Cognition

Embodiments of the methods of the invention further comprise methods of monitoring the effect of a medication or treatment on a subject for treating cognitive impairment and/or age-related dementia, the method comprising comparing cognitive function before and after treatment. Those having ordinary skill in the art recognize that there are well-known methods of evaluating cognitive function. For example, and not by way of limitation, the method may comprise evaluation of cognitive function based on medical history, family history, physical and neurological examinations by clinicians who specialize dementia and cognitive function, laboratory tests, and neuropsychological assessment. Additional embodiments which are contemplated by the invention include: the assessment of consciousness, such as using the Glasgow Coma Scale (EMV); mental status examination, including the abbreviated mental test score (AMTS) or mini-mental state examination (MMSE) (Folstein et al., J. Psychiatr. Res 1975; 12:1289-198); global assessment of higher functions; estimation of intracranial pressure such as by fundoscopy.

In one embodiment, examinations of peripheral nervous system may be used to evaluate cognitive function, including any one of the followings: sense of smell, visual fields and acuity, eye movements and pupils (sympathetic and parasympathetic), sensory function of face, strength of facial and shoulder girdle muscles, hearing, taste, pharyngeal movement and reflex, tongue movements, which can be tested individually (e.g. the visual acuity can be tested by a Snellen chart; a reflex hammer used testing reflexes including masseter, biceps and triceps tendon, knee tendon, ankle jerk and plantar (i.e. Babinski sign); Muscle strength often on the MRC scale 1 to 5; Muscle tone and signs of rigidity.

15. Reagents, Devices, and Kits

Also provided are reagents, devices, and kits thereof for practicing one or more of the above-described methods. The subject reagents, devices, and kits thereof may vary greatly.

Reagents and devices of interest include those mentioned above with respect to the methods of preparing plasma-comprising blood product for transfusion into a subject in need hereof, for example, anti-coagulants, cryopreservatives, buffers, isotonic solutions, etc.

Kits may also comprise blood collection bags, tubing, needles, centrifugation tubes, and the like. In yet other embodiments, kits as described herein include two or more containers of blood plasma product such as plasma protein fraction, such as three or more, four or more, five or more, including six or more containers of blood plasma product. In some instances, the number of distinct containers of blood plasma product in the kit may be 9 or more, 12 or more, 15 or more, 18 or more, 21 or more, 24 or more 30 or more, including 36 or more, e.g., 48 or more. Each container may have associated therewith identifying information which includes various data about the blood plasma product contained therein, which identifying information may include one or more of the age of the donor of the blood plasma product, processing details regarding the blood plasma product, e.g., whether the plasma product was processed to remove proteins above an average molecule weight (such as described above), blood type details, etc. In some instances, each container in the kit includes identifying information about the blood plasma contained therein, and the identifying information includes information about the donor age of the blood plasma product, e.g., the identifying information provides confirming age-related data of the blood plasma product donor (where such identifying information may be the age of the donor at the time of harvest). In some instances, each container of the kit contains a blood plasma product from a donor of substantially the same age, i.e., all of the containers include product from donors that are substantially the same, if not the same, age. By substantially the same age is meant that the various donors from which the blood plasma products of the kits are obtained differ in each, in some instances, by 5 years or less, such as 4 years or less, e.g., 3 years or less, including 2 years or less, such as 1 year or less, e.g., 9 months or less, 6 months or less, 3 months or less, including 1 month or less. The identifying information can be present on any convenient component of the container, such as a label, an RFID chip, etc. The identifying information may be human readable, computer readable, etc., as desired. The containers may have any convenient configuration. While the volume of the containers may vary, in some instances the volumes range from 10 ml to 5000 mL, such as 25 mL to 2500 mL, e.g., 50 ml to 1000 mL, including 100 mL to 500 mL. The containers may be rigid or flexible, and may be fabricated from any convenient material, e.g., polymeric materials, including medical grade plastic materials. In some instances, the containers have a bag or pouch configuration. In addition to the containers, such kits may further include administration devices, e.g., as described above. The components of such kits may be provided in any suitable packaging, e.g., a box or analogous structure, configured to hold the containers and other kit components.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, portable flash drive, etc., on which the information has been recorded. Yet another means that may be present is a website address which may be used via the internet to access the information at a removed site. Any convenient means may be present in the kits.

16. Experimental Procedures

The following examples are put forth to provide those of ordinary skill in the art with a complete disclosure and description of how to make and use the present invention, and are not intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is degrees Centigrade, and pressure is at near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995; Immunology Methods Manual (I. Lefkovits ed., Academic Press 1997); and Cell and Tissue Culture: Laboratory Precedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and Clontech.

A. Materials and Reagents.

USP saline was purchased from Hospira (Lake Forest, Ill.). Injections were performed with 27.5 G or 30 G needles, at a volume of 150 µL per injection. Commercially-available PPF ("PPF1") such as those Commercial PPF Preparations described above in 5% solution were stored at 4° C. Commercially-available HAS ("HAS1") such as those Commercial HAS Preparations described above in 5% solution were stored at 4° C.

B. Animal Supply and Husbandry.

The mouse strains NOD.CB17-Prkdcscid/NcrCrl ("NOD-scid," Strain Code 394, Charles River, Mass.) (Bosma, M. et al., The scid mouse mutant. 137 Curr Top Microbiol Immunol 197 (1988)) and NOD scid gamma ("NSG," Strain Code 005557, The Jackson Laboratory, Bar Harbor, Me.) were used. Each mouse was ear punched to designate a unique identification number. All mice were individually housed under specific pathogen-free conditions under a 12-hour light, 12-hour dark cycle, and all animal handling and use was in accordance with IACUC approved standard guidelines.

C. Administration.

Unless described differently below, NSG and NODscid mice were injected with USP saline, 5% PPF1, or 5% HAS1 twice weekly via intravenous tail vein injection (150 µL per injection) for up to 6 months.

D. Open Field

Open field tests were utilized to determine exploratory behavior of the subject mice. The open field test is an empty test arena, usually round or square. The mouse is placed inside a 50 cm×50 cm open filed arena for 15 minutes and the level of the mouse's activity is measured. Rearing time was measured by tracking the duration the forepaws were on the walls of the box. Total distance covered and velocity was also measured for duration of the test. CleverSys TopScan V3.0 (Reston, Va.) was used to track mouse behavior in open field. Open field chambers were constructed by CleverSys.

E. Y-Maze

Mice were allowed to explore two arms of a Y-maze (start+familiar) for 5 minutes. One hour later, mice were allowed to explore all three arms, and total time and number of entries in the arms were recorded.

F. Barnes Maze

Mice were trained on four consecutive days in a modified Barnes maze and given a maximum of 120 seconds to find the escape hole. (See Barnes, C. A., *Memory deficits associated with senescence: A neurophysiological and behavioral study in the rat*, J. COMPARATIVE AND PHYSIOLOGICAL PSYCHOLOGY, 93(1): 74-104 (1979); and for the modified maze, Faizi, M. et al., *Thy1-hAPP(Lond/Swe+) mouse model of Alzheimer's disease displays broad behavioral deficits in sensorimotor, cognitive and social function*, BRAIN BEHAV. 2(2): 142-54, (2012)). The escape hole remained the same for four trials on a training day, but changed between training days. The latency to the escape hole was recorded for each mouse cohort on four separate training days.

G. DCX- and Ki67-Positive Cells

Doublecortin (DCX) is a microtubule□associated protein that is expressed by neuronal precursor cells. It is also expressed by immature neurons in embryonic and adult cortical structures. When they are actively dividing, neuronal precursor cells express DCX. The protein downregulates after two weeks. Because of this association, it is useful as a marker of neurogenesis.

Brain tissue processing and immunohistochemistry was performed on free-floating sections well-described techniques (Luo, J. et al. Glia-dependent TGF-b signaling, acting independently of the TH17 pathway, is critical for initiation of murine autoimmune encephalomyelitis. J. CLIN. INVEST. 117, 3306-3315 (2007)). Mice were anesthetized and perfused with 0.9% saline. Brains were removed and subsequently fixed with phosphate-buffered 4% paraformaldehyde, pH 7.4, at 4° C. before sunk through 30% sucrose for cryoprotection. Brains were subsequently sectioned at 30 µm with a cryomicrotome at −22° C. Sections were stored in cyroprotective medium. The primary antibody used was goat anti-Dcx (Santa Cruz Biotechnology at 1:500 for twice weekly dosing experiments or 1:200 in the three times per week dosing experiments) or rabbit anti-Ki67 (1:500 Abcam). Primary antibody staining was revealed using biotinylated secondary antibodies and the ABCkit (Vector) with diaminobenzidine (DAB, Sigma-Aldrich) or fluorescence-conjugated secondary antibodies. To estimate the total number of Dcx-positive cells per dentate gyrus, immunopositive cells in the granule cell and subgranular cell layer of the dentate gyrus were counted in three coronal hemibrain sections through the hippocampus and averaged.

H. Barnes Maze Test on Aged NSG Mice Treated with Young Plasma, Effluent I, or Effluent II/III Aged NSG mice (aged 12 months), were separated into several groups (all of n=14), and received 150 µL saline, young plasma, Effluent I, or Effluent II/III by tail vein injection prior to initiation of behavior tests. Each separate group was separated into 3 cohorts with each cohort initiated with behavior tests on a different week.

I. Barnes Maze and Cell Survival (BrdU Staining) in Aged NSG Mice Treated Three Times Per Week with Young Plasma or PPF1

Aged (12 months) male NSG mice were treated intravenously via tail vein injection with 150 µL of clarified young human plasma (young plasma), PPF1, or saline three times per week for four weeks. The regimen was changed to twice per week during weeks 5 and 6, which were the behavioral testing weeks.

Prior to treatment, the mice were divided into three cohorts of 13-15 mice each. Each cohort underwent five days of BrdU injections intraperitoneally (i.p.) prior to the start of treatment of young plasma, PPF1, or saline as described above.

During weeks 5 and 6, behavioral testing was performed, and latency to target hole was measured for each mouse in Barnes Maze testing. Each testing session lasted for a maximum of 120 seconds. The event of finding the target hole was recorded using software that determined when the nose of the mouse entered the area defined as the target hole.

At the end of behavioral testing, the animals were sacrificed, and six sections per hippocampus were quantified using brightfield microscope to determine presence of BrdU positive cells within the granule cell layer of the dentate gyrus. As representative sections throughout the different regions of the hippocampus, the average number of BrdU positive cells were multiplied by 72, which was the total number of sections for each animal's hippocampus, in order to give an estimate of the total number of BrdU positive cells.

J. Neurosphere and Cortex Culture Assays

1. Tuj1 and DAPI Staining

Figure 19:
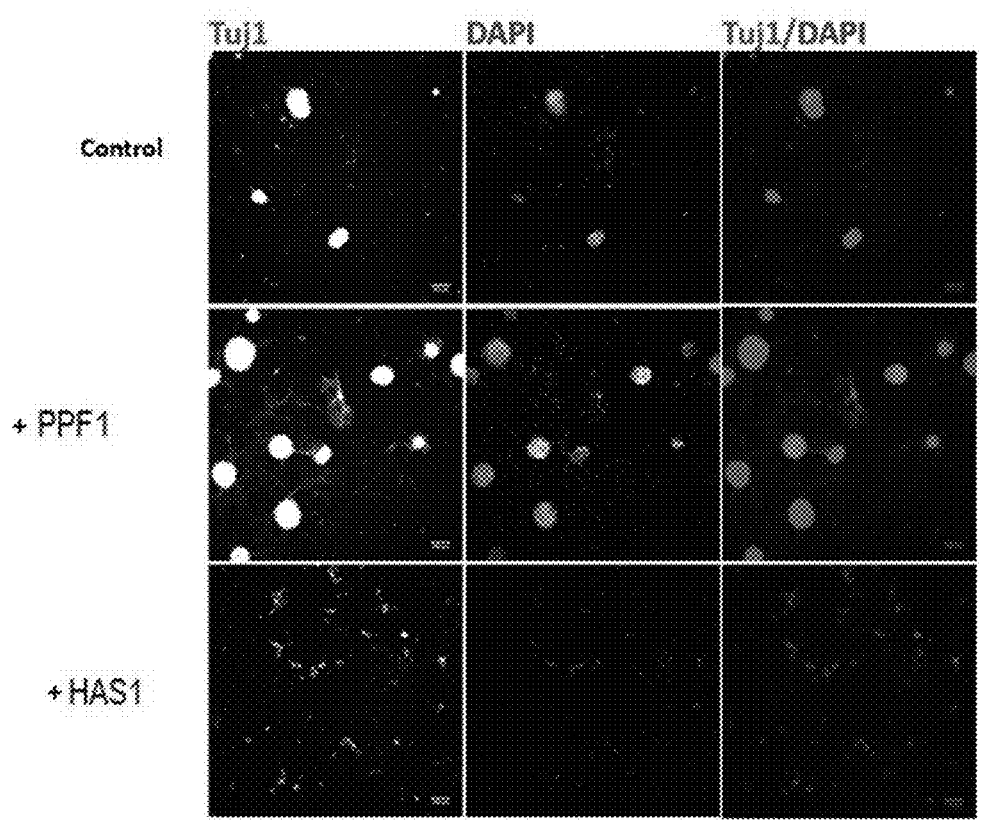
FIG. 19 shows the effects of control, PPF1, and HAS1 on neurosphere proliferation in cortex culture. The figure shows example images of neurospheres from cortical cultures after 21 days in vitro, imaged for Tuj1, DAPI, or Tuj1 and DAPI.

Mouse C57 E14,15 cortices (Lonza: M-CX-300) were suspended in 12 ml of neural basal media supplemented with B27, 2 mM Glutamax (Sigma-Aldrich). 200 µL was added to each well of a 96-well plate pre-coated with collagen I (Corning, Inc.). After 16 hours, plating media was replaced with pre-warmed (37° C.) control media (Neural basal media with B27, 2 mM Glutamax (Gibco). On day 4 in vitro ("days in vitro", or "DIV"), culture media was replaced with fresh control media, control media and 10% PPF1, control media and 10% HAS1, vehicle and 10% PPF1, or vehicle and 10% HAS1. Cultures were maintained for 21 days with 75% of media changed to fresh media every 3 days. At 21 DIV, cultures were washed 3× with PBS then fixed with 4% Paraformaldehyde for 20 minutes at room temperature (RT). After fixation, cultures were washed 2× with PBS then permeabilized with 0.1% Triton X100 for 5-20 minutes. After permeabilization, cultures were blocked with 3% bovine serum albumin (Sigma-Aldrich) for 60 minutes at RT. After 60 minutes, blocking solution was aspirated and cultures were labeled with anti-Tuj1 antibody (AbCam-1:500) at 4° C. overnight. After labeling, cultures were washed 3× with PBS+0.1% BSA then stained with A647-conjugated Donkey anti-mouse antibody at 4° C. overnight (1:1000). Cultures were then washed 2× with PBS and labeled with Hoechst 33342 (1:1000) for 20 min. Samples were washed 3× with PBS after Hoechst labeling. Twenty-five (25) fields were acquired for each well using 10× magnification using GE InCell Analyzer 2000 (GE Healthcare Life Sciences). Results are shown in FIG. 19.

2. Net Neurite Length

Figure 20:
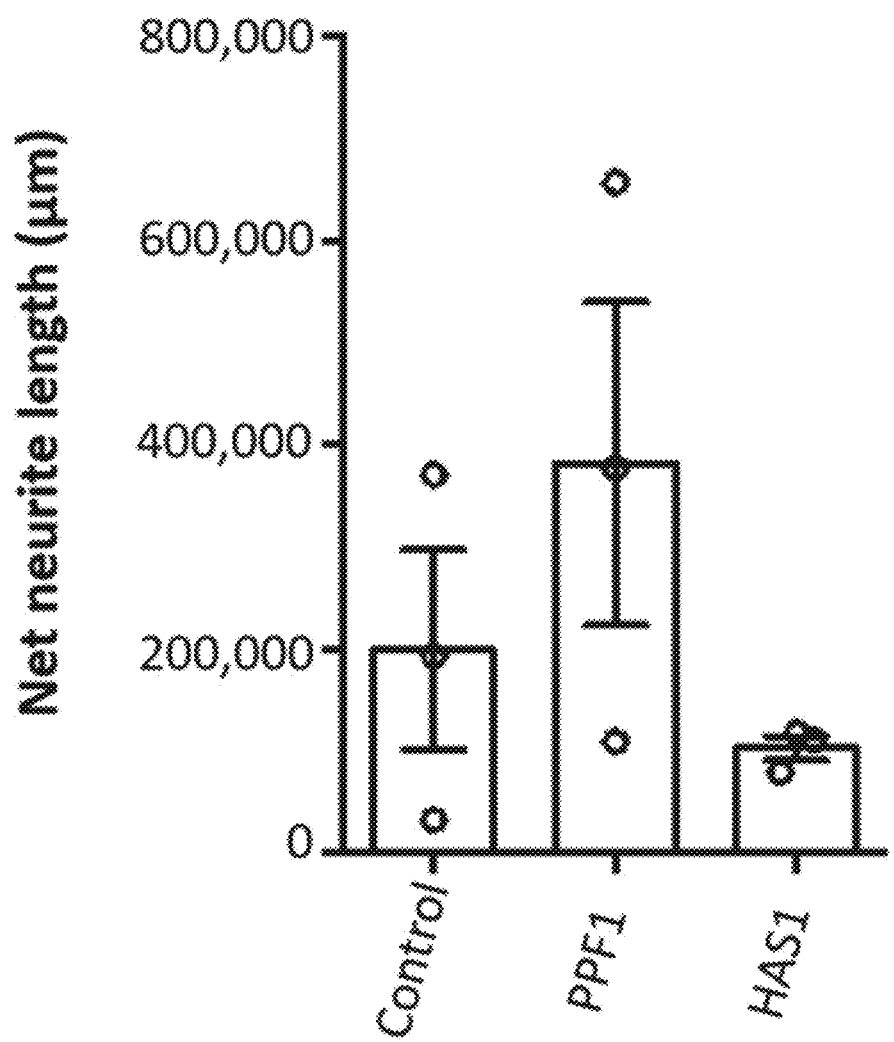
FIG. 20 shows the effects of control, PPF1, and HAS1 on net neurite length in cortex culture.

Net neurite length was determined from cultures as described in the previous section. Neurite analysis was performed using a custom algorithm generated by GE InCell Investigator Developer Toolbox. Results from control and vehicle treated samples were nearly identical therefore were combined for statistical analysis. Results are shown in FIG. 20.

3. Cortex Culture Sphere Number and Size; Process Length and Branching

Mouse C57 E14,15 cortices (Lonza: M-CX-300) were suspended in 12 mL of neurobasal media supplemented with B27, 2 mM Glutamax (Sigma-Aldrich). 200 μL was added to each well of a 96-well plate pre-coated with polylysine and laminin. Four days later, 50% of the media was exchanged with fresh media and treated with test article (vehicle, PPF1, or HAS1) to a final concentration of 10%. This was repeated three days later. On Day 7 of treatment, cells were imaged in phase contrast at 10× magnification with IncuCyte (Ann Arbor, Mich.) and analyzed with standard "Neurite and Cell-Body" algorithms. Six replicates were analyzed with four images taken per replicate. Standard error is displayed. Significance is shown for 2 tailed T-test as P<0.5. Results are displayed in FIGS. 21 and 22.

4. Sox2 Neurosphere Staining

Mouse C57 E14,15 cortical neurons (Lonza: M-CX-300) were suspended in neurobasal media supplemented with B27, 2 mM Glutamax (Sigma-Aldrich) at 100-200K cells/ml. 200 μL was added to each well of a 96-well plate pre-coated with collagen I (Corning, Inc.). After 16 hours, plating media was replaced with pre-warmed (37° C.) control media (Neurobasal media with B27, 2 mM Glutamax (Gibco)). On day 4 in vitro ("days in vitro", or "DIV"), culture media was replaced with fresh control media, control media with HAS vehicle (vehicle), control media and 10% PPF1, control media and 10% HAS1. Cultures were maintained for 21 days with 75% of media changed to fresh media every 3-4 days. At 21 DIV, cultures were washed 3× with PBS then fixed with 4% Paraformaldehyde for 20 minutes at room temperature (RT). After fixation, cultures were washed 2× with PBS then permeabilized with 0.1% Triton 100× for 5-20 minutes. After permeabilization, cultures were blocked with 3% bovine serum albumin (Sigma-Aldrich) for 60 minutes at RT. After 60 minutes, blocking solution was aspirated and cultures were labeled with anti-Tuj1 antibody (AbCam-1:500) and Rabbit anti SOX2 (AbCam: 1:5000 at 4° C. overnight. After labeling, cultures were washed 3× with PBS+0.1% BSA then stained with Donkey anti-mouse-647 (AbCam) and Sheep anti-rabbit-Texas Red at 4° C. overnight (1:1000). Cultures were then washed 2× with PBS and labeled with Hoechst (1:1000) for 20 min. Samples were washed 3× with PBS after Hoechst labeling. Twenty-five (20 or 25) fields were acquired for each well using 10× magnification of InCell Analyzer 2000 (GE Healthcare Life Sciences). Neurosphere and neurite analysis were done using custom algorithm generated by GE InCell Investigator Developer Toolbox. Results from control and vehicle treated samples were nearly identical therefore were combined for statistical analysis. Results are displayed in FIG. 23.

K. Results of In Vivo Experiments

Figure 2:
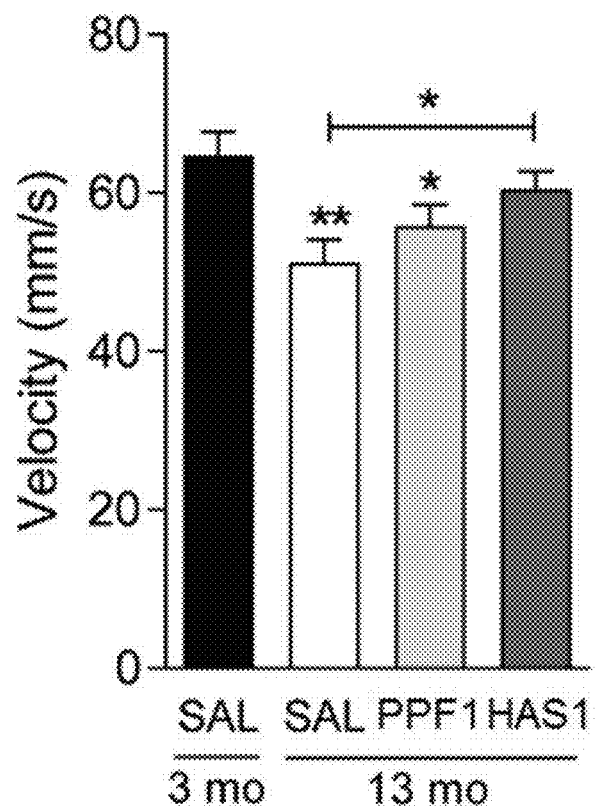
FIG. 2 shows the movement velocity of control, PPF1, or HAS1-treated 3-month or 13-month-old NSG mice that were placed in an Open Field chamber for 15 minutes.
Figure 3:
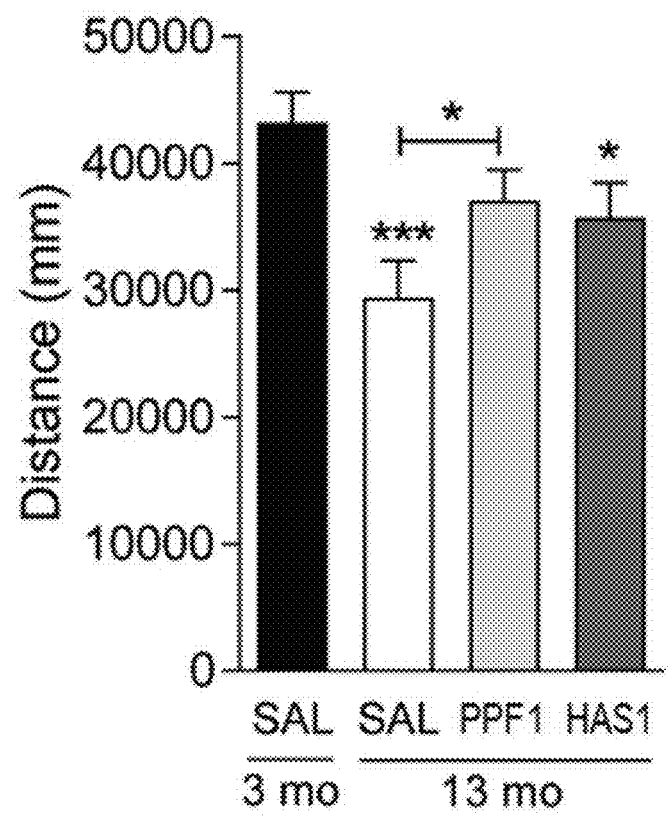
FIG. 3 shows the movement distance traveled of control, PPF1, or HAS1-treated 3-month or 13-month-old NSG mice that were placed in an Open Field chamber for 15 minutes.

1. Open Field Test with 3-month and 13-month-old NSG Mice 3-month (young) or 13-month-old (old) NSG mice were placed in an Open Field chamber for 15 minutes. The time spent rearing FIG. 1, velocity FIG. 2, and distance FIG. 3 were measured. FIG. 1 shows that 13-month-old mice spent less time rearing than 3-month-old mice, but that PPF1 and HAS1-treated mice were not significantly different from young mice. FIG. 2 shows that saline (control) and PPF1-treated 13-month-old mice were significantly slower than 3-month-old mice. However, HAS1-treated mice were significantly faster than saline-treated mice, and not significantly different from young mice. FIG. 3 shows that saline (control) and HAS1-treated old mice had less locomotor activity than young mice, and PPF1-treated mice covered more distance than saline-treated mice. All data shown are mean±s.e.m; *P<0.05; P<0.01; *P<0.001; t-test; n=20, 18, 18, 19. (SAL=saline).

2. Y-Maze Test with 3-Month and 13-Month-Old NSG Mice

Figure 4:
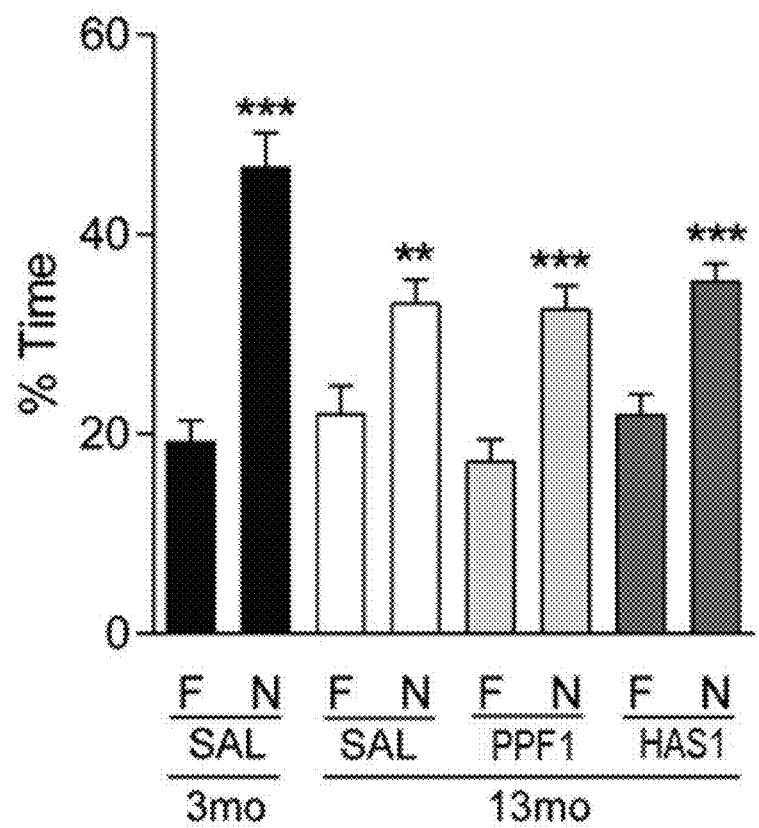
FIG. 4 shows the time spent in the novel arm by 3-month or 13-month-old NSG mice in the cued Y-maze test that were treated with control, PPF1, or HAS1.
Figure 5:
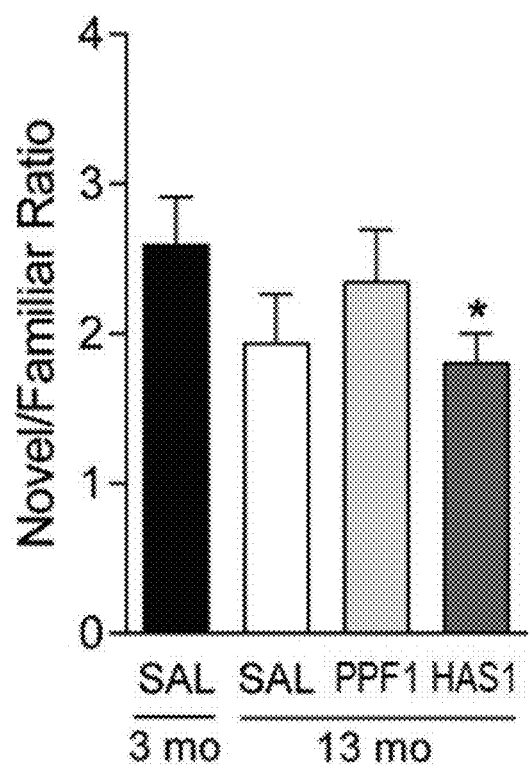
FIG. 5 shows the ratio of time spent by 3-month or 13-month-old NSG mice in the novel versus familiar arms (ratio of novel:familiar) of the cued Y-maze test, the mice having been treated with control, PPF1, or HAS1.
Figure 6:
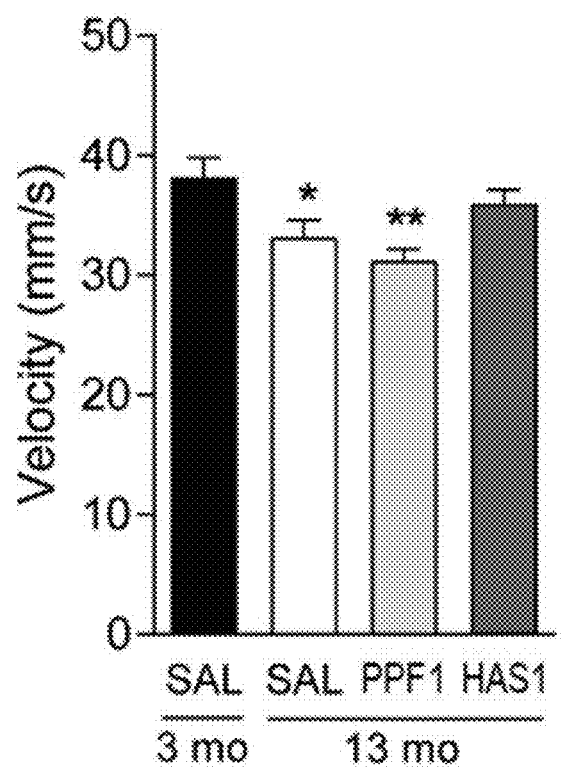
FIG. 6 shows the movement velocity of control, PPF1, or HAS1-treated 3-month or 13-month-old NSG mice in the cued Y-maze test.
Figure 7:
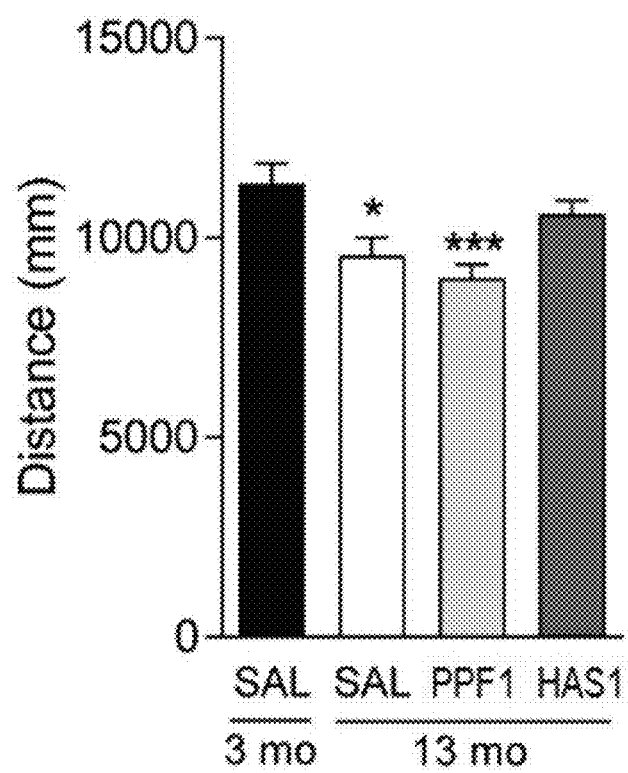
FIG. 7 shows the movement distance traveled of 3-month or 13-month-old NSG mice in the cued Y-maze test, the mice having been treated with control, PPF1, or HAS1.

Young (3-month-old) and old (13-month-old) NSG mice were tested in the cued Y-maze as a test for memory. FIG. 4 shows that all mice spent significantly more time in the novel (N) arm than the familiar (F) arm. FIG. 5 shows that HAS1-treated old mice were significantly impaired in their memory for the familiar arm compared to young mice, whereas PPF1-treated mice trended towards improved memory for the familiar arm. FIG. 6 shows that saline and PPF1-treated, but not HAS1-treated old mice, were significantly slower than young mice. FIG. 7 shows that saline and PPF1-treated, but not HAS1-treated old mice, covered less distance than young mice. All data shown are mean±s.e.m; *P<0.05; P<0.01; *P<0.001; Paired t-test; n=20, 18, 18, 19. (SAL=saline).

3. Fear Conditioning Test for Memory with 3-month and 13-month-old NSG Mice

Figure 8A:
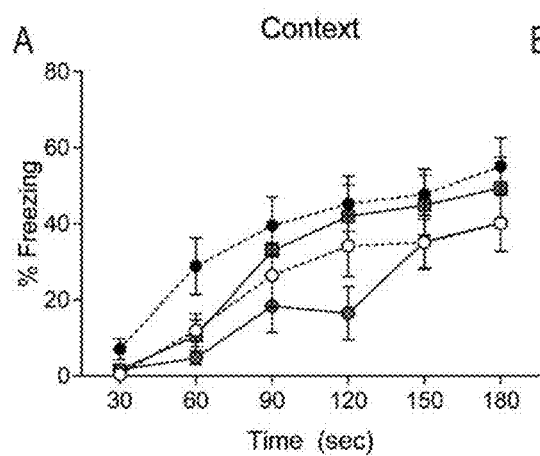
FIG. 8A shows the percent of time freezing in the contextual fear conditioning test for memory by 3-month and 13-month-old NSG mice treated with control, PPF1, or HAS1.
Figure 8B:
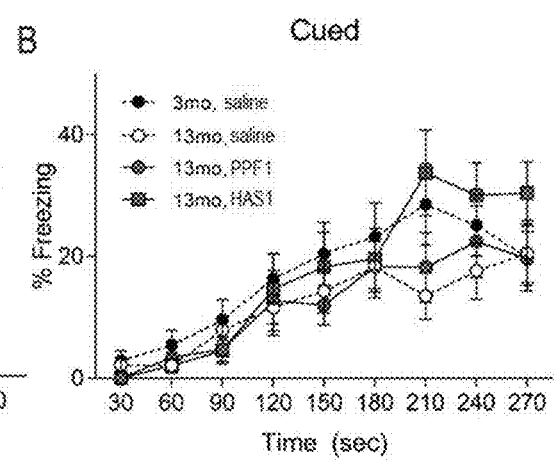
FIG. 8B shows the percent of time freezing in the auditory cued fear conditioning test for memory by 3-month and 13-month-old NSG mice treated with control, PPF1, or HAS1.
Figure 9:
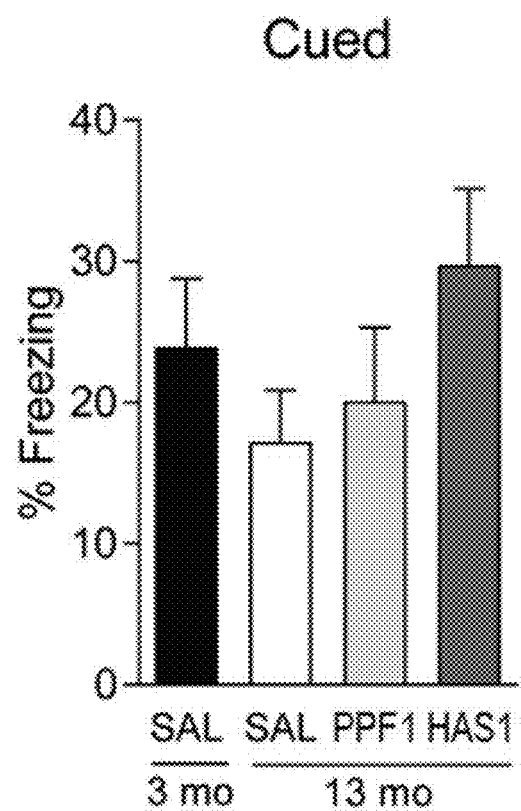
FIG. 9 quantifies percent of time freezing during the last 90 seconds of the cued fear conditioning test for memory in 3-month and 13-month-old NSG mice treated with control, PPF1, or HAS1.

Young (3-month-old) and old (13-month-old) NSG mice were tested in the fear conditioning test for memory. FIG. 8A shows that 13-month-old mice trended to spend less time freezing than 3-month-old mice, whereas HAS1-treated mice spent almost as much time freezing as 3-month-old mice. FIG. 8B shows that in the cued test for memory of the auditory cue, 13-month-old control-treated mice performed the worst and froze the least amount of time. HAS1-treated mice trended to spend more time freezing, indicating improved memory for the tone. FIG. 9 shows the quantification of the last 90 seconds of the cued test for memory and shows that HAS1-treated mice trended to spend more time freezing, indicating improved memory. n=20, 16, 17, 19. (SAL=saline).

4. Barnes Maze Test for Spatial Memory with 3-month and 13-month-old NSG Mice

Young (3-month-old) and old (13-month-old) NSG mice were tested in the Barnes maze test for spatial memory. FIG. 10A shows that 3-month-old mice performed the best and had the fastest latency to reach the target hole by the last trial. FIG. 10B shows the quantification of the average of the last 3 trials which demonstrates that saline- and HAS1-treated old mice were significantly impaired in their memory of the target hole compared to young mice, but the PPF1-treated mice were not significantly different from young mice. $P<0.01$; *$P<0.001$; Unpaired t-test; n=20, 18, 18, 19. (SAL=saline).

5. Immunostaining with 3-month and 13-month-old NSG Mice

Brain sections were stained for doublecortin (Dcx), a marker for newborn neurons or for Ki67, a marker for proliferating cells in 3-month and 13-month-old NSG mice treated twice weekly with saline, PPF1, or HAS1. Dcx- and Ki67-positive cells were counted in the dentate gyrus of young and old NSG mice. FIGS. 11A and 11B respectively show that all old mice had dramatically lower numbers of Dcx- or Ki67-positive cells. PPF1 and HAS1-treated mice trended towards increased numbers of Dcx- and Ki67-positive cells compared to saline-treated mice.

6. Immunostaining with 3-month and 13-month-old NSG Mice Treated Three Times Weekly with PPF1 and HAS1

Figure 12:
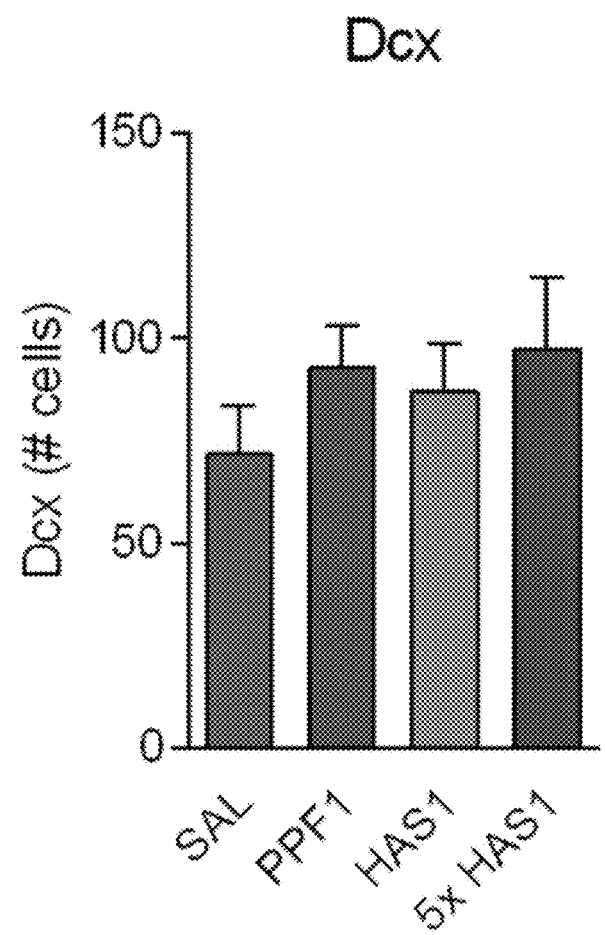
FIG. 12 quantifies the number of cells positively staining for Dcx in 13-month-old NSG mice treated with control, PPF1, 1× concentrated HAS1, or 5× concentrated HAS1 three times per week for five weeks.

Brain sections were stained for doublecortin (Dcx), a marker for newborn neurons or for Ki67, a marker for proliferating cells in 13-month-old mice. The mice were treated three times per week with saline, PPF1, 1× concentrated HAS1, or 5× concentrated HAS1. Dcx- and Ki67-positive cells were counted in the dentate gyrus. FIG. 12 shows that mice treated with PPF1 trended towards an increase in neurogenesis (as indicated by Dcx staining), compared to saline control treated animals. Also shown is that more concentrated HAS1 trended towards increased neurogenesis compared to saline-treated animals.

Figure 13:
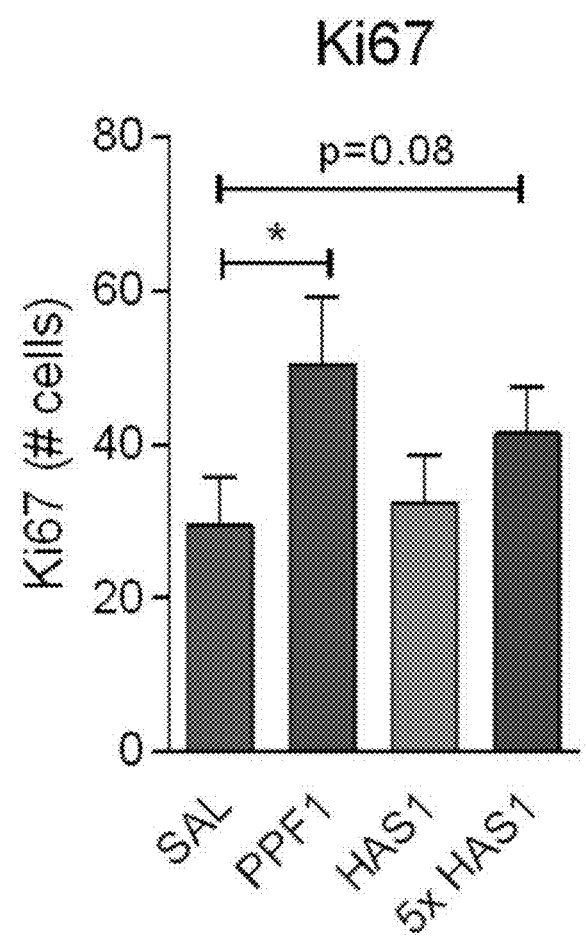
FIG. 13 quantifies the number of cells positively staining for Ki67 in 13-month-old NSG mice treated with control, PPF1, 1× concentrated HAS1, or 5× concentrated HAS1 three times per week for five weeks.

FIG. 13 shows that mice treated with PPF1 had a significant increase in cell proliferation (as indicated by Ki67 staining), compared to saline control treated animals. Also shown is that more concentrated HAS1 trended towards increased neurogenesis compared to saline-treated animals. *$P<0.05$; unpaired t-test against saline group; all data shown are mean±s.e.m.

7. Open Field Test with NODscid Mice

Figure 14A:
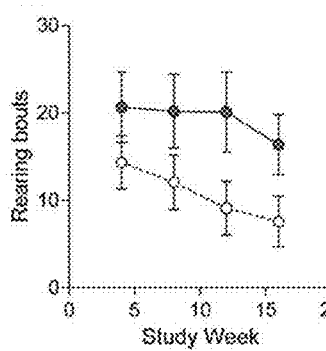
FIG. 14A shows the number of rearing bouts in an Open Field chamber in NODscid mice treated twice weekly via intravenous tail vein injection with either saline (control) or PPF1 starting at 6 months of age. Rearing was measured for a span of 15 minutes once mice were placed in the Open Field chamber.
Figure 14B:
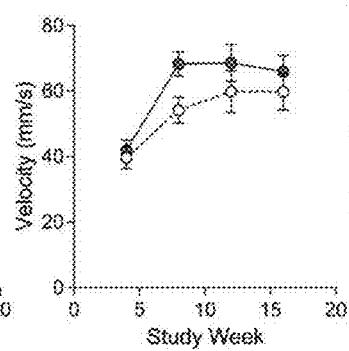
FIG. 14B reports the movement velocity in an Open Field chamber of mice treated twice weekly via intravenous tail vein injection with either saline (control) or PPF1 starting at 6 months of age. Velocity was measured for a span of 15 minutes once mice were placed in the Open Field chamber.
Figure 14C:
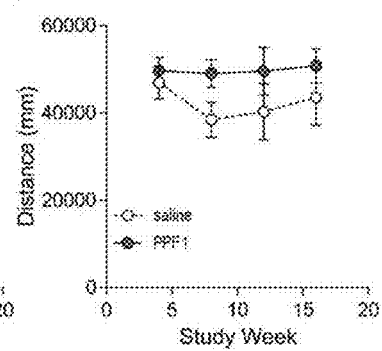
FIG. 14C reports the distance traveled in an Open Field chamber of mice treated twice weekly via intravenous tail vein injection with either saline (control) or PPF1 starting at 6 months of age. Velocity was measured for a span of 15 minutes once mice were placed in the Open Field chamber.

NODscid mice were treated twice weekly via intravenous tail vein injection with either saline or PPF1 starting at 6 months of age. The starting number of mice were 20 for each group. Mice were placed in the Open Field chamber for 15 minutes and locomotor activity was recorded. FIG. 14A shows that PPF1-treated mice trend towards increased rearing activity compared to saline-treated mice. FIGS. 14B and 14C respectively show that PPF1-treated mice also trend towards improved velocity and distance covered compared to saline-treated mice.

Figure 15:
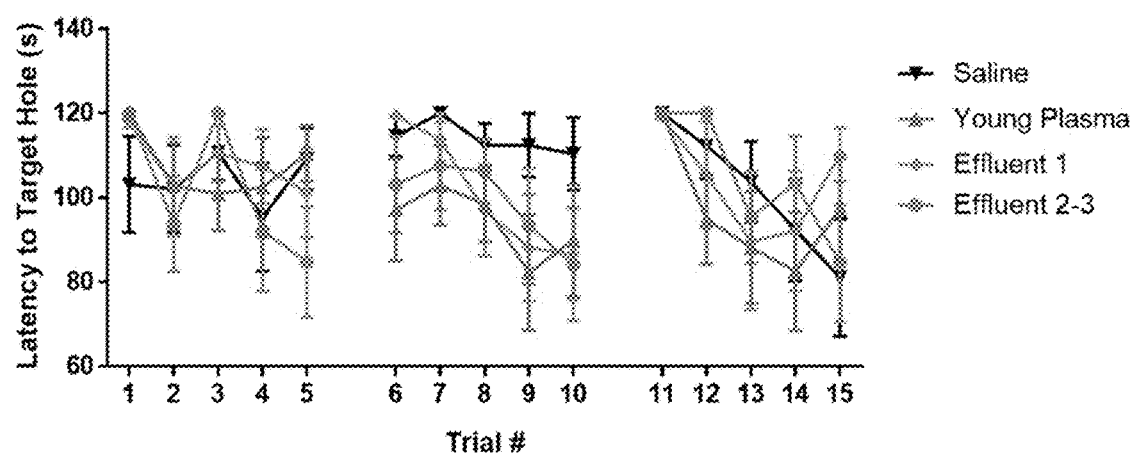
FIG. 15 depicts the Barnes maze latency and hippocampal-dependent spatial learning and memory. The latency to reach the target hole in aged NSG mice (aged 12 months) treated with 150 µL saline control, young plasma, Effluent I, or Effluent II/III is reported.

8. Barnes Maze with Aged (12-month-old) NSG Mice Treated with Young Plasma, Effluent I, and Effluent II/III Aged NSG mice (aged 12 months), were separated into several groups (all of size n=14), and received 150 µL saline, young plasma, Effluent I, or Effluent II/III by tail vein injection prior to initiation of behavior tests. Each separate group was further separated into 3 cohorts with each cohort initiated with behavior tests on a different week. Mice were tested in a modified Barnes Maze (as described above) to assess spatial learning and memory. FIG. 15 shows that treatment with young plasma, Effluent I, or Effluent II/III trended towards significant improvement in latency for aged NSG mice to reach the target hole.

9. Barnes Maze and Cell Survival with Aged NSG Mice Treated with Young Plasma and PPF1

As described above, aged male NSG mice (aged 12 months) were treated with 150 µL of clarified young human plasma (young plasma), PPF1, or saline three times per week (i.v.) for 4 weeks, and then twice per week during weeks 5 and 6, which were the weeks in which testing was performed is reported.

Figure 16:
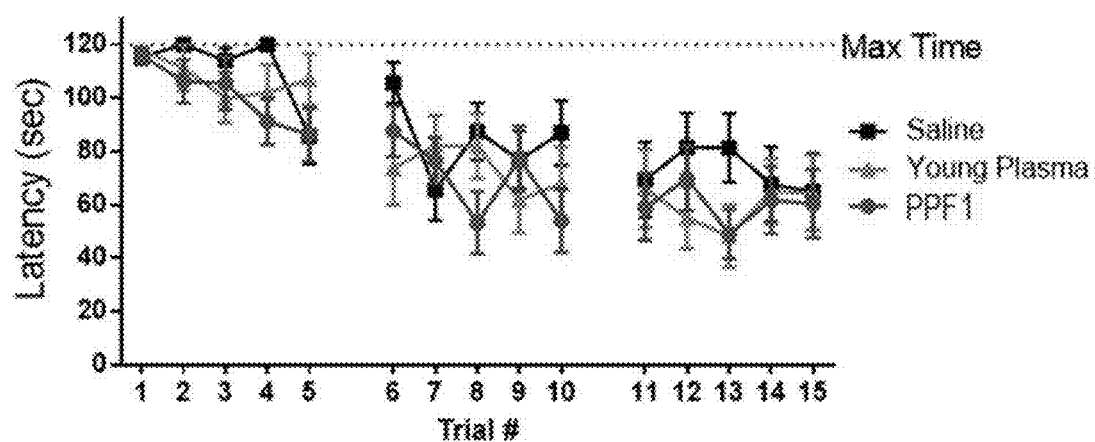
FIG. 16 reports the effect of young human plasma, PPF1, and saline control on hippocampal-dependent spatial learning and memory in male aged NSG mice (aged 12 months). The mice were treated with 150 µL of clarified young human plasma (young plasma), PPF1, or saline three times per week (i.v.) for 4 weeks, and then twice per week during weeks 5 and 6, which were the weeks in which testing was performed is reported. The latency to reach the Barnes Maze hold for each treatment group is reported.

FIG. 16 reports the latency to reach the Barnes Maze hole for each treatment cohort. Treatment with PPF1 significantly improved spatial memory in aged mice compared to control, while treatment with young plasma trended towards improved spatial memory compared to control. (n: Saline=12, PPF1=14, young plasma=11). *$P<0.05$; mean±s.e.m.; unpaired T-Test.

Figure 17:
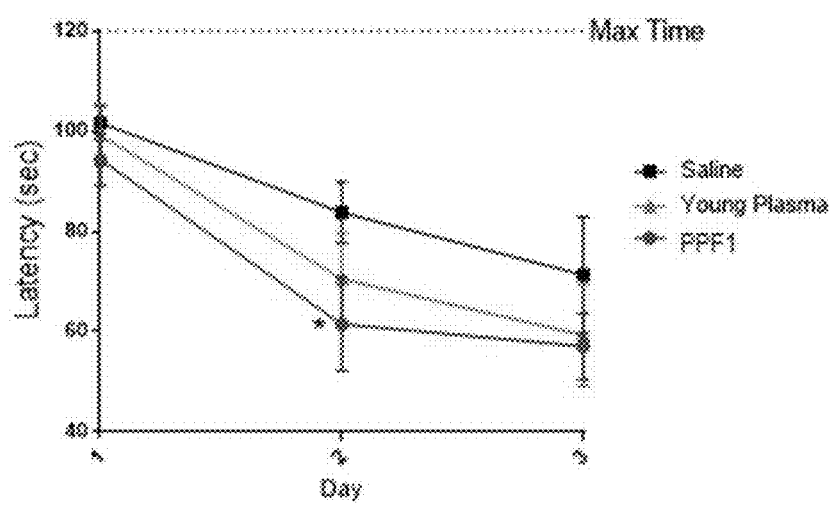
FIG. 17 reports the effect of young human plasma, PPF1, and saline control on the average latency to find the Barnes Maze target hole for the last three trials for each day of testing. Aged NSG mice (aged 12 months) were treated with 150 µL of clarified young human plasma (young plasma), PPF1, or saline three times per week (i.v.) for 4 weeks, and were subsequently treated twice per week during weeks 5 and 6, which were the weeks in which testing was performed.

FIG. 17 reports the average latency to find the target hole for the last three trials for each day of testing. Again, treatment with PPF1 significantly improved spatial memory in aged mice compared to control, while treatment with young plasma trended towards improved spatial memory compared to control. *$P<0.05$; mean±s.e.m.; unpaired T-Test.

Figure 18:
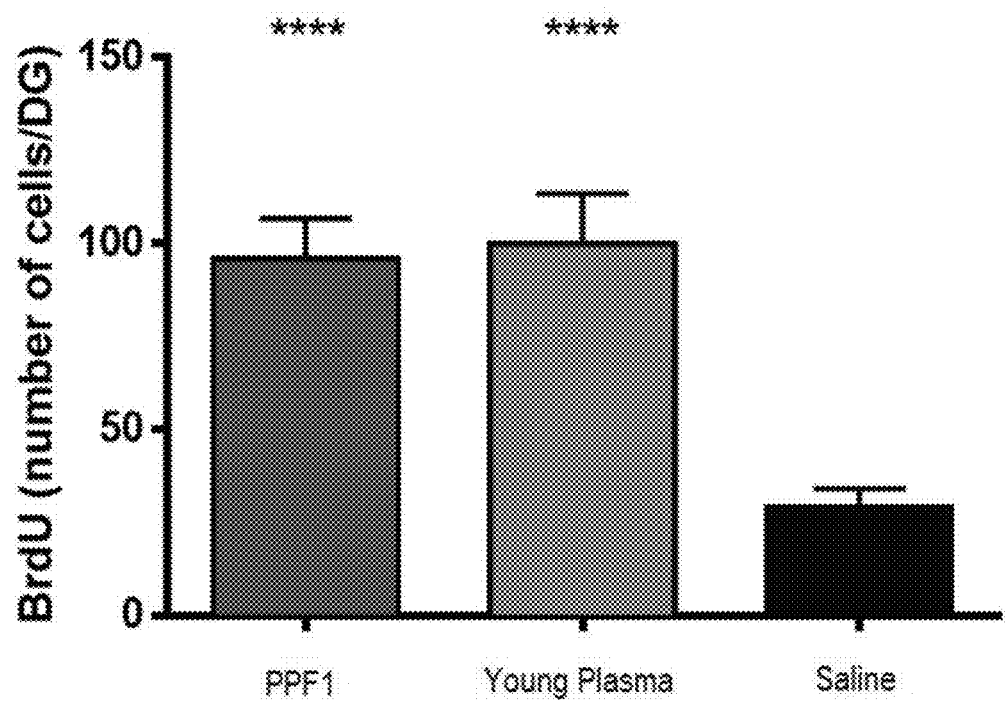
FIG. 18 reports the effect of young human plasma, PPF1, and saline control on cell survival as determined by BrdU detection. Aged NSG mice (aged 12 months) were treated with 150 µL of clarified young human plasma (young plasma), PPF1, or saline three times per week (i.v.) for 4 weeks, and were subsequently treated twice per week during weeks 5 and 6, which were the weeks in which behavioral testing was performed. Hippocampal sections were analyzed after sacrifice.

FIG. 18 reports the effect of young human plasma and PPF1 on cell survival as determined by number of BrdU positively-labeled cells (i.e. proliferating cells) within the granule layer of the dentate gyrus of aged (12 months) NSG mice. BrdU was administered for five days (i.p.) prior to commencing the intravenous injections of young plasma, PPF1, or saline control as described above. A significant increase in cell survival was observed in both young human plasma and PPF1-treated mice compared to saline control. Statistical significance was determined using One-Way ANOVA with Dunnett's multiple comparison post-hoc analysis between PPF1 and young human plasma compared to saline treatment. (n: Saline=13; PPF1=13; young plasma=11, ****$P>0.0001$, Unpaired T-Test between PPF1 or young human plasma and saline treatment).

L. Results of In Vitro Neurosphere and Cortex Culture Assays

FIG. 19 shows that PPF1 and HAS1 differentially modulate neurosphere proliferation in cortex culture. Cortices from E14-15 C57 mice were cultured on collagen I-coated 96-well plates in culture media containing vehicle alone, PPF1 (10%), or HAS1 (10%). Example images of neurospheres from cortical cultures after 21 days in vitro, imaged for Tuj1 (neuron-specific class III beta-tubulin), DAPI (4', 6-diamidino-2-phenylindole), or both TuJ1 and DAPI are shown. FIG. 19 shows that PPF1 increases the amount of neurospheres which express either Tuj1 or DAPI. The increase in Tuj1 expression demonstrates that PPF1-treated cortical cultures produce more neurospheres which have differentiated into a more neuronal-like phenotype.

FIG. 20 depicts three cultures of C57 mouse E14-15 cortical neurons (Lonza: M-CX-300) suspended in neurobasal media supplemented with B27, 2 mM Glutamax (Sigma-Aldrich) at 100-200K cells/mL, coated on collagen I-coated 96-well plates in culture media containing vehicle, PPF1 (10%), or HAS1 (10%). Net neurite length, indicative of neurogenesis, occurred in PPF1-treated cultures compared to control or HAS1-treated cultures.

Figure 21:
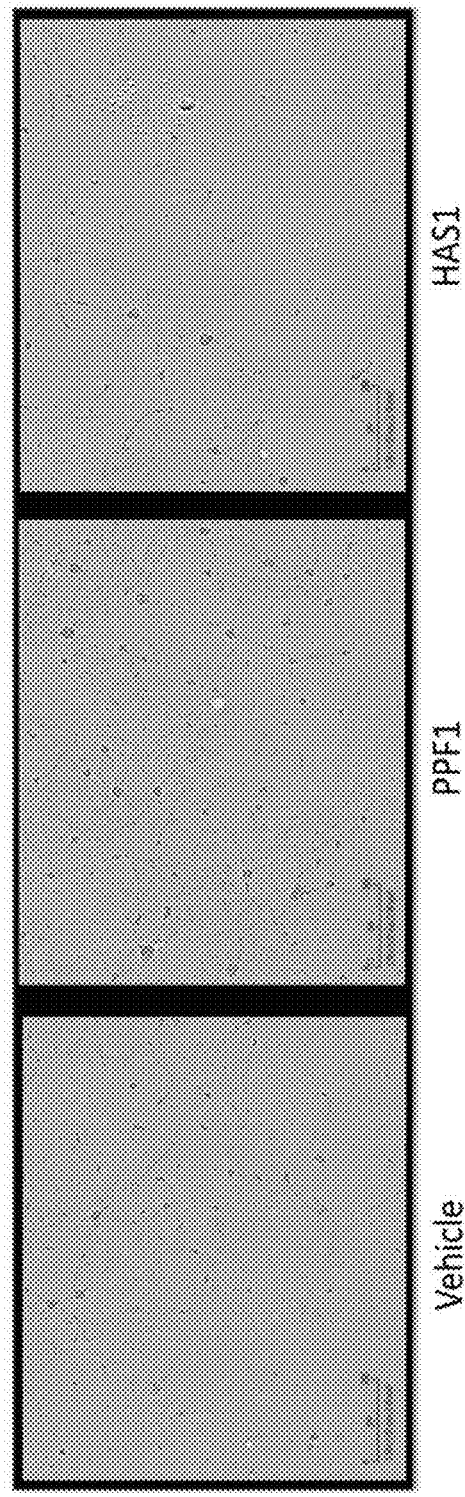
FIG. 21 shows effects of vehicle, PPF1, and HAS1 on sphere and process growth in cortex culture. Yellow shading highlights spheres, and pink shading highlights neurites determined by an IncuCyte software algorithm (Essen Bioscience, Inc., Ann Arbor, Mich.).
Figure 22A:
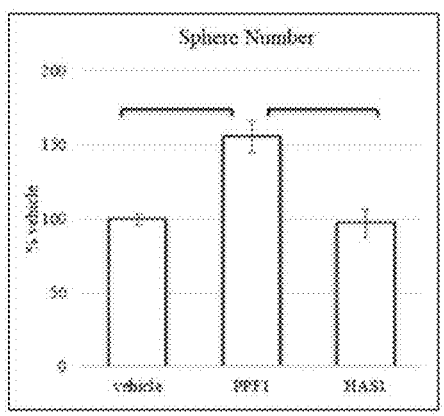
FIG. 22A shows the quantification of neurosphere number as percent of vehicle from cortices from E14-15 mouse embryos suspended in neural basal media supplemented with B27 and 2 mM Glutamax (vehicle), PPF1 (10% of a 5% stock solution), or HAS1 (10% of a 5% stock solution).
Figure 22B:
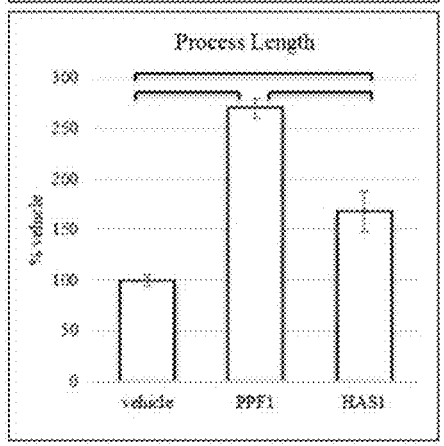
FIG. 22D shows the quantification of neurosphere size as percent of vehicle from cortices from E14-15 mouse embryos suspended in neural basal media supplemented with B27 and 2 mM Glutamax (vehicle), PPF1 (10% of a 5% stock solution), or HAS1 (10% of a 5% stock solution).
Figure 22C:
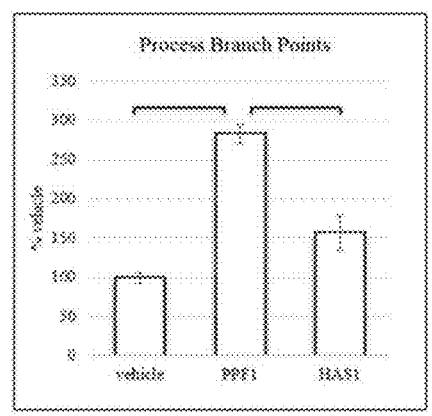
Figure 22D:
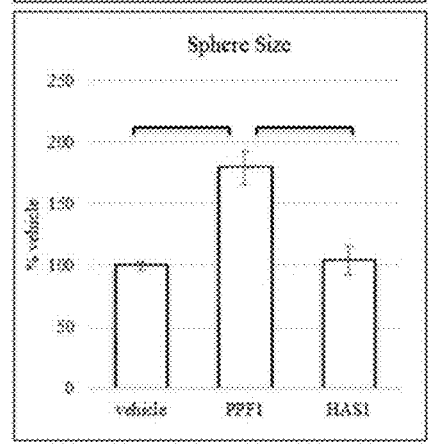

FIG. 21 depicts three cultures of C57 mouse E14-15 cortical neurons (Lonza: M-CX-300) suspended in neurobasal media supplemented with B27, 2 mM Glutamax (Sigma-Aldrich) at 100-200K cells/mL, coated on collagen I-coated 96-well plates in culture media containing vehicle, PPF1 (10%), or HAS1 (10%). An IncuCyte software algorithm available from Essen BioSciences (Ann Arbor, Mich.) detected cortex culture spheres (highlighted in yellow) and processes (highlighted in pink). More spheres and processes were observed in PPF1-treated cultures and increased sphere size and process branching was also observed in PPF1-treated cultures. The scale bars are 300 μm each.

FIG. 22. FIGS. 22A-D report the number of spheres, the process length, process branch points, and sphere size, respectively. Quantification was performed using an IncuCyte software algorithm available from Essen BioSciences (Ann Arbor, Mich.). Standard error is displayed. Significance is shown using a 2-tailed T-Test. FIG. 22A shows that PPF1-treated cultures have an increased number of spheres compared to vehicle or HAS1-treated cultures. (P=0.0006, PPF1 vs. vehicle; P=0.0007, PPF1 vs. HAS1). FIG. 22B shows that PPF1-treated cultures display increased process length compared to vehicle or HAS1-treated cultures. (P=$4e^{-8}$, PPF1 vs. vehicle; P=0.002, PPF1 vs. HAS1; and P=0.018, HAS1 vs. vehicle). FIG. 22C shows that PPF1-treated cultures produce more process branch points compared to vehicle or HAS1-treated cultures. (P=0.002 PPF1 vs. vehicle; P=0.004, PPF1 vs. HAS1). FIG. 22D shows that PPF1-treated cultures are associated with increased sphere size compared to vehicle or HAS1-treated cultures. (P=0.002 PPF1 vs. vehicle; P=0.004, PPF1 vs. HAS1). Together, the results of this data indicate that PPF1 (and HAS1 to a less significant degree) treatment are associated with characteristics indicative of increased cortex culture cellular growth and process formation.

Figure 23:
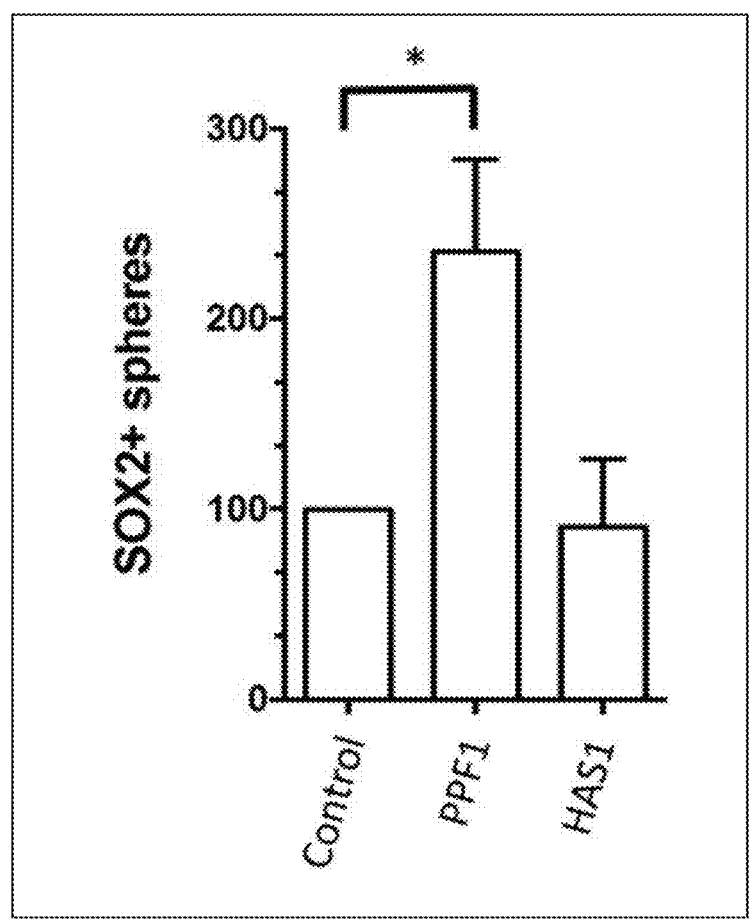
FIG. 23 shows the quantification of the number of neurospheres staining positive for Sox2, which were treated with control vehicle (neural basal media supplemented with B27 and 2 mM Glutamax), PPF1 (10% of a 5% stock solution), or HAS1 (10% of a 5% stock solution). Sox2 staining is an indicator of a neurosphere's potential for neurogenesis.

FIG. 23 displays the number of neurospheres staining positive for Sox2, a transcription factor which plays an important role in maintaining embryonic and neural stem cells. Quantification was performed using a GE InCell Investigator Toolbox algorithm. PPF1-treated cultures produced a significantly increased number of neurospheres staining positive for Sox2, indicating that PPF1 treatment is associated with an increase in number of cells with the potential for neurogenesis.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed:

1. A method of treating a cognitive disorder, comprising intravenously administering an effective amount of a plasma protein fraction (PPF) to a subject diagnosed with a cognitive disorder to treat the subject for the cognitive disorder, wherein the PPF has a total protein content that consists of at least 83 percent but less than 95 percent albumin and no more than 17 percent globulins.

2. The method of claim 1 wherein no more than 1 percent of the total protein shall be gamma globulin.

3. The method of claim 1 further comprising monitoring the subject for improved cognitive function.

4. The method of claim 1 wherein the PPF is produced from a mammalian blood product.

5. The method of claim 4 wherein the mammalian blood product is a human blood product.

6. The method of claim 1 wherein the subject is a mammal.

7. The method of claim 6 wherein the mammal is a human.

8. The method according to claim 1 wherein the method consists of intravenously administering an effective amount of the PPF to the subject to treat the subject for the cognitive disorder.

* * * * *